United States Patent
Hauptmeier et al.

(10) Patent No.: US 8,980,318 B2
(45) Date of Patent: Mar. 17, 2015

(54) NERAMEXANE MULTIPLE UNIT DOSAGE FORM

(75) Inventors: Bernhard Hauptmeier, Gelnhausen (DE); Brigitte Purmann, Mühlheim (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/806,255

(22) PCT Filed: Jun. 22, 2011

(86) PCT No.: PCT/EP2011/003098
§ 371 (c)(1),
(2), (4) Date: Feb. 19, 2013

(87) PCT Pub. No.: WO2011/160839
PCT Pub. Date: Dec. 29, 2011

(65) Prior Publication Data
US 2013/0142870 A1 Jun. 6, 2013

Related U.S. Application Data

(60) Provisional application No. 61/398,393, filed on Jun. 24, 2010.

(30) Foreign Application Priority Data

Jun. 24, 2010 (EP) .................................. 10006609

(51) Int. Cl.
*A61K 9/24* (2006.01)
*A61K 9/20* (2006.01)
*A61K 9/28* (2006.01)
*A61K 9/36* (2006.01)
*A61K 31/13* (2006.01)
*A61K 9/50* (2006.01)

(52) U.S. Cl.
CPC ............... *A61K 31/13* (2013.01); *A61K 9/2027* (2013.01); *A61K 9/2846* (2013.01); *A61K 9/5026* (2013.01); *A61K 9/5078* (2013.01)
USPC ........... 424/472; 424/465; 424/474; 424/480; 514/579

(58) Field of Classification Search
None
See application file for complete search history.

(56) References Cited

U.S. PATENT DOCUMENTS

| | | | |
|---|---|---|---|
| 6,194,000 B1 * | 2/2001 | Smith et al. | .................. 424/458 |
| 2006/0002999 A1 | 1/2006 | Yang et al. | |
| 2007/0141148 A1 | 6/2007 | Hauptmeier et al. | |

FOREIGN PATENT DOCUMENTS

| WO | WO2006/058059 | 6/2006 |
|---|---|---|
| WO | WO2006/138227 | 12/2006 |
| WO | WO2009/033649 | 3/2009 |

OTHER PUBLICATIONS

International Search Report for PCT/EP2011/003098 Of Jul. 14, 2011.

* cited by examiner

*Primary Examiner* — Jeffrey T Palenik
(74) *Attorney, Agent, or Firm* — Hueschen and Sage

(57) ABSTRACT

Unit comprising neramexane, a pharmaceutically acceptable salt, solvate, conjugate, prodrug, polymorphic form, isomer, or derivative thereof; and a release-controlling excipient; wherein said unit has a diameter of from 0.1 to less than 6 mm.

11 Claims, 4 Drawing Sheets

US 8,980,318 B2

NERAMEXANE MULTIPLE UNIT DOSAGE FORM

FIELD OF THE INVENTION

The invention relates to modified release dosage forms of neramexane. Said modified release dosage forms may be multiple unit dosage forms such as tablets, granules and pellets. Such forms are in particular suitable for oral administration.

BACKGROUND OF THE INVENTION

Neramexane, also known as 1-amino-1,3,3,5,5-pentamethylcyclohexane, has been found to be useful in the therapy of various diseases including tinnitus disease. Neramexane appears to be therapeutically effective after oral administration. Typically, neramexane is administered at least twice a day during continuous therapy in order to ensure that therapeutically effective plasma concentrations are maintained and fluctuation of the plasma levels is limited.

Modified release solid oral dosage forms permit the modified release of the active ingredient over an extended period of time in an effort to maintain therapeutically effective plasma levels over similarly extended time intervals and/or to modify other pharmacokinetic properties of the active ingredient.

WO 2007/062815 A1 suggests an oral modified release dosage form comprising a therapeutically effective amount of neramexane, and at least one release-controlling excipient.

WO 2007/009691 suggests mixtures of specific pyrazole derivatives in combination with an anti-addictive agent such as neramexane in the form of microtablets.

EP 1 684 729 suggests a multilayer pharmaceutical form for controlled active ingredient release. Neramexane is mentioned as active ingredient among a variety of other compounds.

US 2007/0231397 A1 suggests pharmaceutical forms having a stable active ingredient release profile. Neramexane is mentioned as active ingredient among a variety of other compounds.

US 2008/0312587 A1 suggests a system for orally administering a solid to dementia sufferer. The antidementia agent may be neramexane.

WO 2009/033649 relates to interval and/or maintenance therapy employing neramexane, wherein neramexane may be introduced into microspheres or microcapsules e.g. based on polyglycolic acid.

US 2007/0141148 relates to oral modified release dosage forms of neramexane.

US 2006/002999 relates to immediate release dosage forms of 1-aminocyclohexanes such as neramexane.

WO 2006/058059 relates to methods and compositions for administering an NMDA receptor antagonist such as memantine to a subject.

WO 2006/138227 relates to immediate release dosage forms containing memantine.

Modified release dosage forms are also known from other active agents. Minitablets comprising a release-controlling excipient are e.g. known from Orfiril®, an agent for the treatment of primary (idiopathic) epilepsy.

Release dosage forms are available either as single unit (nondivided formulation) or as multiple unit (divided formulation) dosage forms. The single unit dosage forms usually refer to diffusion-controlled systems where the drug is dissolved or dispersed throughout a solid matrix and the release of the drug is controlled or sustained either by incorporating a suitable filler within the matrix or by coating the matrix with swellable or nonswellable polymer film(s). The former case is known as a monolithic system where the diffusion of a drug through a matrix is the rate-limiting step. In monolithic preparations made of polymers the drug release is commonly governed by the swelling rate of the polymer matrix. In the second case, the diffusion of the drug through the polymer coating or layer of the system is the rate controlling step.

Multiple unit dosage forms are essential where drug-excipient or drug-drug interaction are possible in a single unit formulation. They are also known to have less variance in transit time through the gastrointestinal tract than single unit dosage forms. The multiple unit dosage forms usually are based on subunits such as granules, pellets, or minitablets. They are usually delivered in hard gelatin capsules or transformed into tablets that disintegrate immediately in aqueous media of the GI tract, releasing the modified release units.

Multiple unit dosage forms may offer advantages and disadvantages over the single unit systems. On the one hand, multiple unit forms may offer more predictable gastric emptying, gastric emptying less dependent on the state of nutrition, a high degree of dispersion in the digestive tract, less variability of absorption, and a lower risk of dose dumping. On the other hand, multiple unit preparations may exhibit several disadvantages. Their manufacturing is more complicated and more expensive, the filling of gelatin capsules is difficult to accomplish especially in the case where different subunits are involved, and the preparation process of minitablets necessitates extra care and fine adjustments of tabletting machines.

Although the debate on the particular advantages of the two formulations (single- and multiple unit) has been going on for a long time in the literature, it has not produced any definite conclusion on the performance of those formulations until now, and the differences in behavior are controversial (AAPS PharmSciTech. 2000; 1(4): article 34).

OBJECTS OF THE INVENTION

Due to the high solubility of neramexane in aqueous media over a wide pH-range and the high permeability in the human gastro intestinal tract a challenging and continual need exists for a modified release formulation containing neramexane or a pharmaceutically acceptable salt thereof facilitating a reliable slow absorption over a targeted period of time. In particular, there is a need for modified release dosage forms of neramexane which are suitable for once-daily administration, and which are well-tolerated, thus rendering unnecessary a repeated administration. Furthermore, there is a need for modified release dosage forms of neramexane which are robust, and whose dissolution behavior does not depend on the state of digestion or dosage form transit through the gastrointestinal tract.

SUMMARY OF THE INVENTION

These objects are achieved by at least one unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm.

In one embodiment, the unit is in the form of a tablet, granule, or pellet; or a combination of two or more thereof.

In one embodiment, the unit is not in the form of a granule.

In another embodiment, the unit is not in the form of a pellet.

In one embodiment, the diameter of the unit is from 0.1 to 5 mm, or is from 0.2 to 4.5 mm, or is from 0.5 to 2.5 mm.

In another embodiment, the weight of the unit is from 0.1 to 100 mg, or from 0.1 to 20 mg, or from 1 to 15 mg, or from 2 to 10 mg.

In one embodiment, said pharmaceutically acceptable salt is neramexane mesylate.

According to a first aspect, the invention provides at least one unit comprising a solid matrix consisting of neramexane, a pharmaceutically acceptable salt, solvate, conjugate, prodrug, polymorphic form, isomer, or derivative thereof; and at least one release-controlling excipient; wherein said solid matrix is coated with said at least one release-controlling excipient; and wherein said unit has a diameter of from 0.1 to less than 6 mm.

According to a second aspect, the invention provides at least one unit comprising a solid matrix comprising neramexane, a pharmaceutically acceptable salt, solvate, conjugate, prodrug, polymorphic form, isomer, or derivative thereof embedded or dispersed in said solid matrix; and at least one release-controlling excipient; wherein said solid matrix is coated with said release-controlling excipient; wherein said unit has a diameter of from 0.1 to less than 6 mm.

According to a third aspect, the invention provides at least one unit comprising a solid matrix comprising neramexane, a pharmaceutically acceptable salt, solvate, conjugate, prodrug, polymorphic form, isomer, or derivative thereof; and at least one release-controlling excipient; wherein said neramexane, a pharmaceutically acceptable salt, solvate, conjugate, prodrug, polymorphic form, isomer, or derivative thereof is embedded or dispersed in said release-controlling excipient; wherein said unit has a diameter of from 0.1 to less than 6 mm.

According to a fourth aspect, the invention provides at least one unit comprising a solid matrix comprising neramexane, a pharmaceutically acceptable salt, solvate, conjugate, prodrug, polymorphic form, isomer, or derivative thereof; and at least one release-controlling excipient; wherein said neramexane, a pharmaceutically acceptable salt, solvate, conjugate, prodrug, polymorphic form, isomer, or derivative thereof is embedded or dispersed in said at least one release-controlling excipient; wherein said solid matrix is coated with a release-controlling excipient; wherein said release-controlling excipients may be the same excipients or may be different from each other; and wherein said unit has a diameter of from 0.1 to less than 6 mm.

According to a fifth aspect, the invention provides at least one unit comprising a solid matrix comprising neramexane, a pharmaceutically acceptable salt, solvate, conjugate, prodrug, polymorphic form, isomer, or derivative thereof deposited on said solid matrix; and at least one release-controlling excipient; wherein said solid matrix comprising said deposited neramexane, a pharmaceutically acceptable salt, solvate, conjugate, prodrug, polymorphic form, isomer, or derivative thereof is coated with said release-controlling excipient; wherein said unit has a diameter of from 0.1 to less than 6 mm.

In one embodiment, the invention provides at least one unit according to the first, second, fourth or fifth aspect, wherein the coating thickness is from 1 to 500 μm, e.g. from 1 to 100 μm, or from 5 to 75 μm, or from 25 to 50 μm, or from 50 to 500 μm, or from 75 to 400 μm, or from 100 to 350 μm, or from 150 to 300 μm.

In one embodiment of the invention, the release-controlling excipient is a water-swellable polymer.

In one embodiment, said release-controlling excipient is a polymer selected from methylcellulose, ethylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, carboxymethyl ethylcellulose, polysaccharides and their derivatives, cellulose acetate phthalate, polyalkylene oxides, polyoxyethylenoxide polymers polyethylene glycols, chitosan, alginate, carrageen, galactomannan, tragacanth, agar, acacia, gellan, guar gum, gum arabicum, gum tragacanth, locust bean gum, xanthan gum, pectin, shellack, carboxymethyl amylopectin, chitosan, maleic anhydride copolymers, polyacrylate, polymethacrylate, methacrylate copolymer, polyvinyl alcohol, polyvinylpyrrolidone, polyvinylpyrrolidone-polyvinyl acetate copolymer and blends of polyvinylpyrrolidone and polyvinyl acetate, poly(2-ethyl-2-oxazoline), poly(ethyleneimine), polyurethane hydrogels, crosslinked polyacrylic acids and their derivatives, and mixtures of any of these.

In one embodiment, said release-controlling excipient is selected from a polyacrylate and/or a polymethacrylate, optionally comprising ammonia acrylate moieties and/or ammonia methacrylate moieties; or from a physical mixture of polyvinyl acetate and polyvinylpyrrolidone; or from a hydroxypropyl methylcellulose; or from a mixture of two or more thereof.

In one embodiment, said release-controlling excipient comprises talc.

In one embodiment, the weight ratio of said release-controlling excipient and said neramexane, a pharmaceutically acceptable salt, solvate, conjugate, prodrug, polymorphic form, isomer, or derivative thereof in said unit is from 15:1 to 13:1.

In one embodiment, said release-controlling excipient is selected such that in application not more than 80% by weight of said active agent are released from said tablet within a period of 1 hours, as determined according to European Pharmacopeia, EP 5.

In one embodiment, not more than 50% by weight are released.

According to a sixth aspect, the invention provides a modified release dosage form which comprises at least one unit according to the invention.

In one embodiment, said modified release dosage form is a multiple unit dosage form.

In another aspect, the invention provides a tablet comprising at least two units according to the invention, wherein said unit is a granule and/or a pellet.

According to another aspect, the invention provides a capsule or stickpack, comprising at least one unit or the modified release dosage form according to the invention, or a tablet comprising at least two units according to the invention, wherein said unit is a granule and/or a pellet.

According to a seventh aspect, the invention relates to a unit according to the first, second, fourth or fifth aspect, wherein said at least one release-controlling excipient used for said coating comprises at least one first and at least one second release-controlling excipient, which are different from one another.

In one embodiment, the unit is the unit according to the second aspect of the invention.

In one embodiment, said at least one first release-controlling excipient and said at least one second release-controlling excipient are polymers selected from polyacrylate and/or polymethacrylate.

In one embodiment, said polyacrylate and/or polymethacrylate is/are an ionic polyacrylate and/or ionic polymethacrylate.

In another embodiment, said at least one first release-controlling excipient is a polymer selected from polyacrylate, polymethacrylate and/or ethylcellulose; and said at least one second release-controlling excipient is a polymer selected from methylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, carboxymethyl ethylcellulose, polysaccharides and their derivatives, cellulose acetate phthalate, polyalkylene oxides, polyoxyethylenoxide polymers, polyethylene glycols, chitosan, alginate, carrageen, galactomannan, tragacanth, agar, acacia, gellan, guar gum, gum arabicum, gum tragacanth, locust bean gum, xanthan gum, pectin, shellack, carboxymethyl amylopectin, chitosan, maleic anhydride copolymers, polyvinyl alcohol, polyvinylpyrrolidone, polyvinylpyrrolidone-polyvinyl acetate copolymer and blends of polyvinylpyrrolidone and polyvinyl acetate, poly (2-ethyl-2-oxazoline), poly(ethyleneimine), polyurethane hydrogels, crosslinked polyacrylic acids and their derivatives; copolymers of the aforementioned polymers including block copolymers and graft polymers; lipids and waxes including, for example, beeswax, natural or synthetic mono-, di- and triglycerides of medium and long chain fatty acids such as hydrogenated vegetable oils, carnauba wax, petroleum wax, microcrystalline wax, long chain fatty acids, long chain fatty alcohols, esters of fatty acids and fatty alcohols; and mixtures of any of these compounds.

In one embodiment, said at least one first release-controlling excipient as defined in section [0048] is a polymer selected from polyacrylate and/or polymethacrylate.

In one embodiment, said poly(meth)acrylate is a non-ionic poly(meth)acrylate.

In one embodiment, said non-ionic poly(meth)acrylate is an ester of poly(meth)acrylate.

In one embodiment, said at least one second release-controlling excipient according to the embodiments as defined in sections [0048] to [0051] is hydroxypropylmethylcellulose.

In another embodiment, said at least one first release-controlling agent is ethylcellulose.

In another embodiment, said at least one first release-controlling agent is ethylcellulose; and said at least one second release-controlling excipient is a polyvinyl alcohol or a polyvinyl acetate or a polyvinyl alcohol grafted with polyethylene glycol.

In one embodiment, the weight ratio of the at least one first release-controlling excipient to the at least one second release-controlling excipient is in the range of from 20:1 to 1:1; or from 15:1 to 2:1.

In another embodiment, the weight of the at least one first release-controlling excipient ranges from 2 to 25% or 5 to 20% based on the total weight of the unit.

In another embodiment, said coating further comprises a sub-coating, an anti-sticking agent and/or a plasticizer.

DETAILED DESCRIPTION OF THE INVENTION

Terms as Used in this Disclosure

The term "capsule" encompasses a case enclosing a dose of medication.

The term "conjugate" encompasses a product, wherein neramexane is covalently or non-covalently attached to a carrier.

The term "deposited on" comprises an embodiment, wherein the active agent is positioned only on the surface of a solid matrix, and/or an embodiment, wherein the active agent partially penetrates from the surface into the interior of the solid matrix.

The term "derivative thereof" encompasses neramexane wherein the amino group is derivatized with one or two alkyl groups.

The term "diameter" defines the longest diameter of the unit, e.g. the longest diameter of the tablet, the granule or the pellet.

The term "excipient" encompasses an inactive substance (compound, agent, ingredient) which is used as a carrier for the active agent. The term "excipient" also encompasses a pharmaceutically acceptable, physiologically inactive ingredient such as a binder, a filler, a coating-forming compound, a plasticizers for coatings, a compound which masks odors, and the like. Examples of further optional excipients are pigments, flavors, sweeteners, opacifiers, anti-adhesives, preservatives, glidants, lubricants, sorbents. Suitable substances are known in the art.

The term "form" encompasses the type of formulation, which is described by its appearance and the shape of the dosage form to be administered to a patient via a defined application route.

The term "granule" encompasses aggregates of particles, e.g. powder particles, to form a multiparticle entity. In pharmaceutical terms, a granule encompasses small particles gathered into a larger, permanent aggregate in which the original particles may still be identified. Granules may be obtained in a granulation process, in which powder particles adhere to each other by different physical mechanisms. Processes such as thermoplastic granulation, aqueous or organic solvent based pot granulation, granulation in a tumbling mixer, granulation in a fluidized bed granulator, granulation by spray drying or dry granulation by compaction are known in the field of pharmaceutical compositions.

The term "immediate release" defines a release rate in which at least 80% of the active agent are released after 30 min. Experimental conditions for measuring the release are the conditions as defined in U.S. Pharmacopoeia, e.g. USP 32, or European Pharmacopoeia, e.g. EP 5.

The term "independent" in connection with release of the active agent means that the in-vitro release profiles of two tablets or matrices do not differ by more than about 10% of the incorporated dose at any point of time after the initial phase of drug release (0 to 1 hour).

The term "ingredient" is used simultaneously with the expressions active, active ingredient, active substance, active moiety meaning the pharmacologically active substance in the formulation, e.g. neramexane mesylate.

The term "isomers" encompasses possible stereoisomers of neramexane such as conformational isomers and enantiomers or diastereomers.

The term "modified release dosage form" encompasses a dosage form from which an incorporated active compound (or agent or ingredient or substance) is released slowly over a period of time as defined in detail below. The term encompasses a pharmaceutical formulation comprising a therapeutically effective amount of neramexane and pharmaceutically acceptable salts, solvates, conjugates, prodrugs, polymorphic forms, isomers, or derivatives thereof, and at least one release controlling excipient. The term encompasses a form which may be orally administered to a patient in need thereof.

The term "multiple unit" encompasses at least two entities such as at least two single tablets, at least two granules, and at least two pellets.

The term "multiple unit dosage form" encompasses a dosage form which consists of at least two units which contain the effective amount of neramexane, or which consist of the effective amount of neramexane.

The term "neramexane" refers to 1-amino-1,3,3,5,5-pentamethylcyclohexane as well as to a pharmaceutically acceptable salt or salts, a solvate or solvates, a conjugate or conjugates, a prodrug or prodrugs, a polymorphic form or polymorphic forms, an isomer or isomers, and derivative or derivatives thereof.

The term "pellet" encompasses a spherical particle typically created by special granulation technologies. A pellet may be produced by layering active material on a starter particle or by extrusion and spheronisation or by pelletizing in a fluidized bed or by thermal melting, forming, cooling processes. Such processes for producing pellets are known in the field of pharmaceutical formulation development.

The term "pharmaceutically acceptable" in connection with an ingredient (or substance or compound or agent) encompasses an ingredient (or a substance or compound or agent) which does not affect the safety of a human being and/or is well-tolerated by a human being after administration.

The term "polymorphic form" encompasses neramexane, a pharmaceutically acceptable salt, solvate, conjugate, prodrug, isomer, or derivative thereof forming different crystal structures or lattices.

The term "prodrug" encompasses a substance that is derived from neramexane or a substance from which neramexane may be prepared in vivo, and which is administered in an inactive or less active form compared to neramexane itself.

The term "protect" means prevent delay or treat, or all, as appropriate, development or continuance or aggravation of a disease in a subject.

The term "release-controlling excipient" defines an agent, which is capable of decreasing the release rate of an active compound from a dosage form or formulation such as a tablet, a granule or a pellet, relative to the dissolution of said active ingredient per se, i.e. in an immediate release environment where no retardation of the release of the active ingredient is achieved.

The term "salt" encompasses the product of the reaction of 1-amino-1,3,3,5,5-pentamethylcyclohexane with an acid thus forming said salt.

The term "single unit" encompasses one entity such as a single tablet, a single granule, and a single pellet.

The term "single unit dosage form" defines a dosage form which consists only of one unit which contains the effective amount of neramexane, or which consists of the effective amount of neramexane.

The term "solid matrix" defines any material in which the active agent may be dispersed or embedded, or on which the active agent may be coated. The solid matrix may comprise or consist of the excipients and release-controlling excipients as defined above. The solid matrix may also consist of the active agent.

The term "solvate" encompasses a product, wherein 1-amino-1,3,3,5,5-pentamethylcyclohexane is associated with molecules of a solvent, or attracts such molecules. If the solvent is water, the solvate is also termed as "hydrate".

The term "stickpack" defines a small tubular bag enclosing a dose of medication.

The term "tablet" defines any solid pharmaceutical composition comprising the active ingredient. The term encompasses both compressed formulations and non-compressed formulations. Non compressed formulation can be manufactured e.g. by thermal or melting processes. The tablet may have any shape, which is common in the field of tablets, such as a round shape, a rectangular shape or an oval shape, or a convex shape, or the shape of a disk, or the shape of a bead. The shape may also be irregular. The term also comprises the term "minitablet" and "microtablet". Such term is known in the field of pharmaceutical compositions. A tablet may be made from granules and/or pellets. The processing of granules and or pellets into tablets is known to a person skilled in the art.

The term "talc" or "talcum" encompasses a mineral composed of hydrated magnesium silicate having the chemical formula $H_2Mg_3(SiO_3)_4$ or $Mg_3Si_4O_{10}(OH)_2$. In loose form, it is well known as talcum powder. The use thereof in pharmaceutics is known. It may e.g. be used as anti-sticking agent.

The term "taste masking coating" defines a coating which does not substantially influence the drug release profile of the modified release matrix. In other words, except perhaps in the initial phase of drug release, there will be no substantial difference at any time between the dose fraction released from an uncoated matrix and an identically formulated and processed matrix which has a taste masking coating. Again, a substantial difference is understood as a difference of 10% or more of the dose of active compound incorporated in the matrix. It is believed that the greatest impact of a taste masking coating on the shape of the drug release profile is in the initial phase of drug release, such as during the first 15 or 30 minutes, which is not relevant to the overall release characteristics of a modified release dosage form.

The term "therapeutically effective amount" is defined as the amount of active ingredient considering factors such as the specific disease condition, which is treated, the dosing regimen, the patient's disease state and the weight of the patient etc. A "therapeutically effective amount" means the amount of a compound that, when administered to a mammal for treating a state, disorder or condition is sufficient to effect such treatment. The "therapeutically effective amount" will vary depending on the compound, the disease and its severity and the age, weight, physical condition and responsiveness of the mammal to be treated. According to the instant invention, in one embodiment, a therapeutically effective amount of neramexane is an amount effective to treat tinnitus. In another embodiment, a therapeutically effective amount is an amount effective to treat neuropathic pain, or other painful conditions such as visceral hypersensitivity. Other uses include, but are not limited to, the treatment of dementia and depression. The effective amount of the drug for pharmacological action, and therefore the tablet strength, depends on the disease itself.

The term "treat" means to relieve or alleviate at least one symptom of a disease in a subject, including for example, tinnitus. The term may mean to relieve or alleviate the intensity and/or duration of a manifestation of disease experienced by a subject in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognitive impairment. Within the meaning of the present invention, the term "treat" also denotes to arrest, delay the onset (i.e., the period prior to clinical manifestation of a disease) and/or reduce the risk of developing or worsening a disease.

The term "unit" encompasses an entity which contains neramexane and a release-controlling excipient, or which consists of neramexane and a release-controlling excipient. Such unit is defined as a tablet, a granule, or a pellet; or such unit or entity is a tablet, a granule, or a pellet; or has the form of a tablet, granule or pellet.

Ratios and proportions relate to weight ratios and weight proportions if not otherwise indicated.

General Aspects of the Invention

The invention provides a modified release dosage form comprising a therapeutically effective amount of an active compound selected from neramexane and a pharmaceutically acceptable salt, solvate, conjugate, prodrug, polymorphic form, isomer, or derivative thereof, and at least one release controlling excipient.

In one embodiment, the release dosage form is a single unit dosage form.

In another embodiment, the release dosage form is a multiple unit dosage form.

Specifically, the invention provides a modified release dosage such as a multiple unit dosage form comprising a therapeutically effective amount of neramexane, and at least one release-controlling excipient.

More specifically, the invention provides at least one unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm.

In one embodiment, the unit is a tablet, a granule, or a pellet; or is in the form of a tablet, granule, or pellet.

The multiple unit dosage form comprises at least two tablets, at least two granules (i.e. two pieces or particles of the granulate material), and/or at least two pellets.

In one embodiment, the invention provides a modified release dosage form comprising at least one unit such as a tablet, a granule and/or a pellet comprising a pharmaceutical composition comprising as an active agent neramexane, a pharmaceutically acceptable salt, solvate, conjugate, prodrug, polymorphic form, isomer, or derivative thereof, and a release-controlling excipient, wherein said unit, e.g. a tablet, granule and/or pellet, has a diameter of from 0.1 to less than 6 mm.

In one embodiment, said unit, e.g. a tablet, granule and/or pellet, has a diameter of from 0.1 to 5 mm.

In another embodiment, said unit, e.g. a tablet, granule and/or pellet, has a diameter of from 0.2 to 4.5 mm.

In still another embodiment, said unit, e.g. a tablet, granule and/or pellet, has a diameter of from 0.5 to 2.5 mm.

The measurement of the diameter may be performed according to methods which are known in the art, e.g. by microscopical methods or by a caliper gauge.

In one embodiment, said unit, e.g. a tablet, granule and/or pellet, has a weight ranging from 0.1 to 100 mg.

In another embodiment, said unit, e.g. a tablet, granule and/or a pellet, has a weight of from 0.1 to 20 mg.

In another embodiment, said unit, e.g. a tablet, granule and/or a pellet, has a weight of from 1 to 15 mg.

In still another embodiment, said unit, e.g. a tablet, granule and/or a pellet, has a weight of from 2 to 10 mg.

In one embodiment, the release-controlling excipient is a water-swellable and/or water-insoluble and/or porous polymer. Suitable polymers are generally known to the person skilled in the art. Examples include cellulose polymers and their derivatives including, but not limited to, methylcellulose, ethylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, carboxymethyl ethylcellulose, cellulose acetate phthalate, polysaccharides and their derivatives, polyalkylene oxides, polyoxyethylenoxide polymers polyethylene glycols, chitosan, alginate, carrageen, galactomannan, tragacanth, agar, acacia, gellan, guar gum, gum arabicum, gum tragacanth, locust bean gum, xanthan gum, pectin, shellack, carboxymethyl amylopectin, chitosan, maleic anhydride copolymers, polyacrylate, polymethacrylate, methacrylate copolymer, polyvinyl alcohol, polyvinylpyrrolidone, polyvinylpyrrolidone-polyvinyl acetate copolymer and blends of polyvinylpyrrolidone and polyvinyl acetate, poly(2-ethyl-2-oxazoline), poly(ethyleneimine), polyurethane hydrogels, crosslinked polyacrylic acids and their derivatives, and mixtures of any of these.

Further suitable compounds and polymers are release-controlling lipids and waxes including, for example, beeswax, natural or synthetic mono-, di- and triglycerides of medium and long chain fatty acids such as hydrogenated vegetable oils, carnauba wax, petroleum wax, microcrystalline wax, long chain fatty acids, long chain fatty alcohols, esters of fatty acids and fatty alcohols etc.

Further examples are copolymers of the polymers listed above, including block copolymers and graft polymers. Specific examples of copolymers are commercially available polyethylene oxide-polypropylene oxide block copolymers such as known under the trademark Pluronic® and Tectonic® (BASF). Further examples are commercially available hydrolyzed starch polyacrylonitrile graft polymers, commonly known as "Super Slurper" (Illinois Corn Growers Association).

Release-controlling excipients based on polyvinylpyrrolidone are commercially available e.g. under the trademark Kollidon (BASF), e.g. Kollidon SR. Kollidon SR comprises a physical mixture of polyvinyl acetate and polyvinylpyrrolidone. Specifically, Kollidon SR comprises a mixture of 80% polyvinyl acetate and 19% polyvinylpyrrolidone. The mixture contains about 0.8% sodium lauryl sulfate and 0.2% silica (by weight).

Release-controlling excipients based on polymethacrylate and/or polymethacrylate-copolymers are e.g. commercially available under the trademark Eudragit. Grades are e.g. Eudragit RS 30 D, Eudragit RL 30 D, Eudragit NE 40 D, Eudragit RS PO and Eudragit NE 30 D, or a combination of two or more thereof.

Eudragit RS 30 D contains from 6.11 to 8.26% ammonia methacrylate moieties based on dry substance determined according to Ph. Eur. 2.2.20. Eudragit RL 30 contains from 10.18 to 13.73% ammonia methacrylate moieties based on dry substance determined according to Ph. Eur. 2.2.20. Eudragit RS PO contains from 4.48 to 6.77% ammonia methacrylate moieties based on dry substance determined according to Ph. Eur. 2.2.20. Eudragit NE 30 D is a neutral copolymer of ethyl acrylate with methyl methacrylate.

Among the above-mentioned water-swellable polymers, some may be considered non-ionic polymers, such as non-ionic cellulose ether. An example of such polymers is hydroxypropyl methylcellulose (HPMC), also called hypromellose, which may be used alone or in combination with other polymers.

Different grades of hydroxypropyl methylcellulose according to the invention include commercially available grades such as HPMC 2208, HPMC 2906 and HPMC 2910. These grades differ in their degree of substitution both with regard to the methyl (or methoxyl) and hydroxypropyl (or hydroxypropoxyl) groups. In HPMC 2208, an average of approx. 22% (range: 19 to 24%) of the original hydroxyl groups of the cellulose have been reacted into methoxyl groups, and an average of approx. 8% (range: 7 to 12%) have been reacted into hydroxypropoxyl groups. HPMC 2906 comprises approx. 29% methoxyl groups and approx. 6% hydroxypropoxyl groups, and HPMC 2910 comprises approx. 29% methoxyl groups and approx. 10% hydroxypropoxyl groups.

A typical grade of hydroxypropyl methylcellulose is HPMC 2208, which is e.g. commercially available as Methocel K 100M CR.

Hydroxypropylcellulose is e.g. commercially available under the trademark Klucel.

Ethylcellulose is e.g. commercially available under the trademark Surelease®. Exemplarily mentioned types are Surelease® E-7-19010 and E-7-19050.

Another grade is Surelease® E-7-7050. Surelease® E-7-7050 is an ethylcellulose which contains a plasticizer.

The relative amount of water-swellable and/or water-insoluble and/or porous polymer needed to achieve the desired release characteristics depends, inter alia, on the selected polymer type and grade, the presence or absence of other excipients having impact on drug release, and on the desired drug load of the matrix. The ratio of this polymer to the active compound is typically selected in the range from about 20:1 to about 1:20, or from about 15:1 to about 1:15, or from about 10:1 to about 1:10, and may be from about 5:1 to about 1:5. In one embodiment, the ratio of polymer to active compound is about 15:1 to about 13:1. In one embodiment, the ratio is 14:1 (weight/weight).

In one embodiment, the polymer is cellulose ether such as hydroxypropyl methylcellulose.

If a high-viscosity HPMC such as Methocel K 100M CR is chosen as principal release-controlling excipient, a typical ratio between the HPMC and the active compound is from about 4:1 to about 1:4 or from about 2:1 to about 1:2.

Further examples of pharmaceutically acceptable water-swellable and/or water-insoluble and/or porous polymers, lipids and waxes are well-known to the person skilled in pharmaceutical sciences.

In one embodiment, one or more of the above defined release-controlling excipients are used in the unit and modified release dosage form according to the invention.

In one embodiment, said release-controlling excipient comprises talc or is employed in combination with talc.

In one embodiment, neramexane is incorporated in the dosage form of the invention in form of one of its salts. Said salts generally have substantial water solubility.

Potentially suitable salts of neramexane include, but are not limited to, acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, fumaric, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid.

In one embodiment, said addition salt is neramexane mesylate.

Compared to a single unit dosage form or monolithic form comprising the same weight of active agent as a multiple unit dosage form of the invention, the multiple unit dosage form provides an improved retardation since per time unit less active agent is released. While such single unit dosage form distribution and transit time in the human gastro intestinal tract may vary according to disease state, this behavior is, from a statistical perspective, unlikely for multiple unit dosage forms. This is also expected for the impact of food on the transit time of monolithic versus multiple unit dosage forms. Therefore, there is a high probability that the absorption of neramexane is more even in a multiple unit dosage form. Furthermore, plasma concentrations are more evenly and side effects can be minimized.

In one embodiment, said comparison relates to a single unit dosage form or monolithic form and a multiple unit dosage form which are coated with a coating having the same coating thickness.

First Aspect of the Invention

Modified Release Dosage Form, Wherein the Active Agent Forms a Solid Matrix which is Coated with a Release-Controlling Excipient According to a first aspect, the invention provides a modified release dosage form comprising at least one unit, wherein said unit comprises a solid matrix consisting of neramexane, a pharmaceutically acceptable salt, solvate, conjugate, prodrug, polymorphic form, isomer, or derivative thereof; and at least one release-controlling excipient; wherein said solid matrix is coated with said at least one release-controlling excipient; and wherein said unit has a diameter of from 0.1 to less than 6 mm.

According to this first aspect, a unit is provided comprising a solid matrix consisting of neramexane, a pharmaceutically acceptable salt, solvate, conjugate, prodrug, polymorphic form, isomer, or derivative thereof; and at least one release-controlling excipient; wherein said solid matrix is coated with said at least one release-controlling excipient; and wherein said unit has a diameter of from 0.1 to less than 6 mm.

Accordingly, the solid matrix does not contain any excipient.

The unit may be a tablet, a granule or a pellet; or a mixture thereof.

Tablets may be produced by methods which are known in the art, e.g. by compression processes or thermal or melting processes as referred to in the section "Definition of terms".

Typical methods for the preparation thereof include the compression of granules prepared by wet or dry granulation, and the direct compression of powder mixtures into compacts. Wet granulation involves the weighing of neramexane, a pharmaceutically acceptable salt, solvate, conjugate, prodrug, polymorphic form, isomer, or derivative thereof, and compressing the same into tablets.

In dry granulation, the neramexane, a pharmaceutically acceptable salt, solvate, conjugate, prodrug, polymorphic form, isomer, or derivative thereof is weighed and compacted, such as by roller compaction, and subsequently broken up or screened. The screened granules are compressed into tablets.

Granules may be obtained in a granulation process, in which powder particles adhere to each other by different physical mechanisms. Processes such as thermoplastic granulation, aqueous or organic solvent based pot granulation, granulation in a tumbling mixer, granulation in a fluidized bed granulator, granulation by spray drying or dry granulation by compaction may be employed.

A pellet may be produced by layering active material on a starter particle or by extrusion and spheronisation or by pelletizing in a fluidized bed or by thermal melting, forming, cooling processes.

Subsequent to the preparation of the tablet, the granule or the pellet, said at least one unit is coated with said release-controlling excipient.

Appropriate coating processes are known in the field of pharmaceutical formulations.

In one embodiment, said release-controlling excipient is selected from the group consisting of water-insoluble lipids and waxes, water-insoluble and/or water-swellable and/or porous polymers. It is also possible to combine excipients from different chemical sub-groups. The release-controlling excipients as defined above may be used for said coating.

In one embodiment, the polymers used as release-controlling excipient may be provided as organic solutions, organic suspension organic dispersion, aqueous solution, aqueous suspension or aqueous dispersions and sprayed onto tablets using conventional coating equipment. Typically, the coating solution, suspension or dispersion will also contain one or more plasticizers, such as glycerol, propylene glycol, polyethylene glycol, diethyl phthalate, dibutyl phthalate, dibutyl sebacate, triacetin, triethyl citrate, acetyltriethyl citrate, acetyltributyl citrate, castor oil, mono- and diglycerides etc.

In one embodiment, the solid matrix consisting of neramexane, a pharmaceutically acceptable salt, solvate, conjugate, prodrug, polymorphic form, isomer or derivative thereof, may be coated with a fluidized bed coater known in the art. Coating conditions such as air velocity, spray rate, and atomization pressure are typically controlled as appreciated by and known to those skilled in the art. The temperature of the solid matrix may e.g range from about 40° C. to 55° C. The air velocity may range from about 5 to 9 m/s. The spray rates may range from about 9 to 42 gm/min. The atomization pressure may range from about 1.5 to 2.0 bar. Subsequent to the coating, the coated solid matrix may be dried in e.g. a fluidized bed of the coating apparatus at a temperature of about 45° C. to about 50° C. for at least 5 min, or at least 15 min, or at least 30 min.

In case the coating provides adhesive properties, at least a second layer of a polymer may be applied to said first coating that is capable of preventing sticking.

In some cases it is mandatory to place a primary, non functional sub-coating layer on the surface of the matrix formulation. This formulation concept is used, if e.g. the active ingredient interacts with excipients in the functional coating layer or the surface properties of the formulation are inappropriate for a direct coating of a functional coating.

In one embodiment, the release-controlling excipient is based on a polyacrylate or a polymethacrylate or on polyacrylate and/or polymethacrylate-copolymers, which optionally comprise ammonia acrylate moieties and/or ammonia methacrylate moieties. Suitable polymers are e.g. commercially available under the above referred trademarks such as Eudragit. Grades are e.g. Eudragit RS 30 D, Eudragit RL 30 D, Eudragit NE 30 D, Eudragit NE 40 D, Eudragit RS PO, or combinations of two or more thereof.

In one embodiment, the invention relates to a unit such as a tablet, granule or pellet, wherein said unit comprises a solid matrix consisting of neramexane mesylate; wherein said solid matrix is coated with a release-controlling excipient based on a polyacrylate or a polymethacrylate or a polyacrylate copolymer and/or polymethacrylate copolymer, which optionally may contain ammonia acrylate moieties and/or ammonia methacrylate moieties; wherein said unit has a diameter of from 1.5 to 2.5 mm.

In another embodiment, said tablet, granule or pellet is coated with ethylcellulose. In one embodiment, a Surelease grade such as Surelease E-7-7050 is employed.

In another embodiment, said tablet, granule or pellet is coated with a hydroxypropyl methylcellulose (HPMC). Grades as defined above may be used, such as HPMC 2208, HPMC 2906 and HPMC 2910.

In another embodiment, said tablet, granule or pellet is coated with an ethylcellulose such a Surelease® grade as defined above, such as Surelease® E-7-7050.

In another embodiment, said tablet, granule or pellet is coated with a cellulose acetate.

In one embodiment, one or two or more of the above mentioned polymers selected from ethylcellulose; hydroxypropyl methylcellulose; polyvinyl acetate/polyvinylpyrrolidone; cellulose acetate; may be used for the preparation of the coating.

In one embodiment, said release-controlling excipient comprises talc or is employed in combination with talc or talcum powder.

In one embodiment, for preparation of the coating, said release-controlling excipient is mixed with talc or talcum powder. Subsequent to the mixing, the mixture may be applied according to the methods as described above such as spraying.

In one embodiment, the weight ratio of release-controlling agent to talc is from 1:1.5 to 1.5:1, or from 1.25:1 to 1:1.25 or is 1:1.

In one embodiment, said tablet, granule or pellet contains neramexane in an amount of from 2 to 3 mg.

In one embodiment, said tablet, granule or pellet contains said release-controlling excipient in an amount of from 1.0 mg to 3.0 mg.

In one embodiment, the sum of the weight of the release-controlling excipient and talc is from 1.5 mg to 3 mg, or from 1.8 mg to 2.4 mg, or from 2.0 mg to 2.2 mg.

In one embodiment, the total weight of the tablet, granule or pellet ranges from 4 to 10 mg.

The release-controlling excipient or mixture of excipients is selected in an amount sufficient to achieve the release characteristics described herein-below. Depending on its type, the typical content of the excipient is from about 10 wt.-% to about 80 wt.-% based on the total weight of the tablet.

In one embodiment, said tablet, granule or pellet contains neramexane in an amount of from 2 to 3 mg, said release-controlling excipient in an amount of from 1.0 to 3.0 mg, wherein the total weight of the tablet ranges from 4 to 10 mg, or from 4 to 8 mg.

Coating Thickness and Weight of Unit

In one embodiment, the coating thickness of the coating the units such as tablets, granules and/or pellets are coated with, is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

The coating thickness may be determined microscopically, e.g. via cross-sectioning a tablet. Such methods are known to a person skilled in the pharmaceutical formulation sciences.

In one embodiment, the unit, e.g. a tablet, granule or pellet, has a weight of from 0.1 to 100 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 0.1 to 20 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 1 to 15 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 2 to 10 mg, and the coating thickness ranges is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In one embodiment, the weight of the unit, e.g. a tablet, granule or pellet, has a weight of 0.1 to 100 mg, or 0.1 to 20 mg, or 1 to 15 mg, or 2 to 10 mg, and the coating thickness ranges from 1 to 500 µm, e.g. from 1 to 100 µm, or from 5 to 75 µm, or from 25 to 50 µm, or from 150 to 300 µm.

Second Aspect of the Invention
Modified Release Dosage Form, Wherein the Active Agent is Embedded or Dispersed in a Solid Matrix which is Coated with a Release-Controlling Excipient According to a second aspect, the invention provides a modified release dosage form comprising at least one unit, which comprises a solid matrix comprising neramexane, a pharmaceutically acceptable salt, solvate, conjugate, prodrug, polymorphic form, isomer, or derivative thereof, embedded or dispersed in said solid matrix; and at least one release-controlling excipient; wherein said solid matrix is coated with said release-controlling excipient; and wherein said unit has a diameter of from 0.1 to less than 6 mm.

According to this second aspect, at least one unit is provided comprising a solid matrix comprising neramexane, a pharmaceutically acceptable salt, solvate, conjugate, prodrug, polymorphic form, isomer, or derivative thereof embedded or dispersed in said solid matrix; and at least one release-controlling excipient; wherein said solid matrix is coated with said release-controlling excipient; wherein said unit has a diameter of from 0.1 to less than 6 mm.

In one embodiment, no release-controlling excipient is present in the interior of said solid matrix.

In one embodiment, said solid matrix comprises a pharmaceutical composition comprising said active agent neramexane, a pharmaceutically acceptable salt, solvate, conjugate, prodrug, polymorphic form, isomer, or derivative thereof. In one embodiment, said pharmaceutical composition comprises or consists of said active agent and one or more of the excipients as described above which are different from release-controlling excipients. Accordingly, the matrix may comprise the active compound together with excipients and/or further compounds that are commonly used in pharmaceutical formulations.

In one embodiment, said modified dosage form is a multiple unit dosage form.

In one embodiment, the unit is selected from tablets, granules and/or pellets, or a combination of two or three thereof.

Modified Release Dosage Form Based on Tablets

In one embodiment, the invention provides a modified release dosage form comprising at least one unit comprising a pharmaceutical composition comprising as an active agent neramexane, a pharmaceutically acceptable salt, solvate, conjugate, prodrug, polymorphic form, isomer, or derivative thereof, wherein said active agent is embedded or dispersed in a solid matrix; and at least one release-controlling excipient; wherein said solid matrix is coated with said release-controlling excipient; and wherein said unit is a tablet, wherein said unit has a diameter of from 0.1 to less than 6 mm.

Tablets may be produced by methods which are known in the art, e.g. by compression processes or thermal or melting processes as referred to in the section "Definition of terms".

In one embodiment, the matrix is a compressed matrix, i.e. the modified release dosage form is a compressed matrix tablet. Typical methods for the preparation thereof include the compression of granules prepared by wet or dry granulation, and the direct compression of powder mixtures into compacts.

Wet granulation involves the weighing of the ingredients, including the active compound and most of the excipients, plus a liquid binder solution, mixing the ingredients, agglomerating them, screening them damp, drying them, dry screening, lubrication, and compressing the resultant admixture into tablets. Advantages of wet granulation include improvement of the cohesiveness and compressibility of powders, a good particle size distribution suitable for compression, reduction of dust and airborne contamination, and prevention of the segregation of components.

In dry granulation, the ingredients are weighed, mixed and compacted, such as by roller compaction, and subsequently broken up or screened. The screened granules are lubricated and compressed into tablets. Since no liquid binder solution is used for agglomeration, the powder mixture which is granulated in dry form must comprise at least one dry binding agent such as microcrystalline cellulose, polyvinylpyrrolidone, or a co-processed mixture of lactose and microcrystalline cellulose. One of the advantages of dry granulation methods is that they may be suitable for the processing of sensitive materials, such as moisture- or heat-sensitive ingredients, as no water is added during the process and no heating is required for drying the granules.

Grades of microcrystalline cellulose are e.g. known under the trademark Avicel® such as Avicel PH 102.

In one embodiment, said solid matrix comprises a binder selected from starches, sugars, cellulose or modified cellulose such as microcrystalline cellulose or other cellulose derivatives, hydroxypropycellulose, lactose, sugar alcohols such as xylitol, sorbitol, matitol. Binders also include gelatin and polyvinylpyrrolidone.

The formulations may also comprise further ingredients such as untreated fumed silica. An appropriate grade is known under the trademark CAB-O-SIL®, such as CAB-O-SIL M5.

In another embodiment, the solid matrix is prepared as a non-compressed matrix, e.g. by thermal or melt processing the ingredients intended to form said matrix.

Subsequent to the preparation of the solid matrix comprising said active agent, said solid matrix is coated with said release-controlling excipient.

In one embodiment, said release-controlling excipient is selected from the group consisting of water-insoluble lipids and waxes, water-insoluble polymers, and/or water-swellable polymers, and/or porous polymers. It is also possible to combine excipients from different chemical sub-groups. The release-controlling excipients as defined above may be used for said coating.

Appropriate coating processes are known in the field of pharmaceutical sciences.

In one embodiment, the polymers used as release-controlling excipient may be provided as organic solutions, organic suspension organic dispersion, aqueous solution, aqueous suspension or aqueous dispersions and sprayed onto tablets using conventional coating equipment. Typically, the coating solution, suspension or dispersion will also contain one or more plasticizers, such as glycerol, propylene glycol, polyethylene glycol, diethyl phthalate, dibutyl phthalate, dibutyl sebacate, triacetin, triethyl citrate, acetyltriethyl citrate, acetyltributyl citrate, castor oil, mono- and diglycerides etc.

In case the coating provides adhesive properties, at least a second layer of a polymer may be applied to said first coating that is capable preventing sticking.

In some cases it is mandatory to place a primary, non functional sub-coating layer on the surface of the matrix formulation. This formulation concept is used, if e.g. the active ingredient interacts with excipients in the functional coating layer or the surface properties of the formulation are inappropriate for a direct coating of a functional coating.

In one embodiment, the release-controlling excipient is based on a polyacrylate or a polymethacrylate or on polyacrylate and/or polymethacrylate-copolymers, which optionally comprising ammonia acrylate moieties and/or ammonia methacrylate moieties. Suitable polymers are e.g. commercially available under the above referred trademarks such as Eudragit. Grades are e.g. Eudragit RS 30 D, Eudragit RL 30 D, Eudragit NE 30 D, Eudragit NE 40 D, Eudragit RS PO, or combinations of two or more thereof.

Accordingly, in one embodiment, the invention relates to a tablet comprising a pharmaceutical composition comprising as an active agent a pharmaceutically acceptable salt of neramexane such as neramexane mesylate, and as release-controlling excipient a polyacrylate or a polymethacrylate or a polyacrylate copolymer and/or polymethacrylate copolymer, which optionally may contain ammonia acrylate moieties and/or ammonia methacrylate moieties, wherein said active agent is embedded or dispersed in a solid matrix, wherein said solid matrix is coated with said release-controlling excipient, wherein said tablet has a diameter of from 1.5 to 2.5 mm.

In another embodiment, said tablet is coated with ethylcellulose. In one embodiment, a Surelease grade such as Surelease E-7-7050 is employed.

In another embodiment, said tablet is coated with a hydroxypropyl methylcellulose (HPMC). Grades as defined above may be used, such as HPMC 2208, HPMC 2906 and HPMC 2910.

In another embodiment, said tablet is coated with an ethylcellulose such a Surelease® grade as defined above, such as Surelease® E-7-7050.

In another embodiment, said tablet is coated with a cellulose acetate.

In one embodiment, one or two or more of the above mentioned polymers selected from ethylcellulose; hydroxypropyl methylcellulose; polyvinyl acetate/polyvinylpyrrolidone; cellulose acetate; may be used for the preparation of the coating.

Accordingly, in one embodiment, the invention relates to a tablet comprising a pharmaceutical composition comprising as an active agent a pharmaceutically acceptable salt of neramexane such as neramexane mesylate and as release-controlling excipient one or more of the following: ethylcellulose; hydroxypropyl methylcellulose; polyvinyl acetate/polyvinylpyrrolidone; cellulose acetate; wherein said active agent is embedded or dispersed in a solid matrix; wherein said solid matrix is coated with said release-controlling excipient; and wherein said tablet has a diameter of from 1.5 to 2.5 mm.

In one embodiment, said release-controlling excipient comprises talc or is employed in combination with talc or talcum powder.

In one embodiment, for preparation of the coating, said release-controlling excipient is mixed with talc or talcum powder. Subsequent to the mixing, the mixture may be applied according to the methods as described above such as spraying.

In one embodiment, the weight ratio of release-controlling agent to talc is from 1:1.5 to 1.5:1, or from 1.25:1 to 1:1.25 or is 1:1.

In one embodiment, said tablet contains neramexane in an amount of from 2 to 3 mg.

In one embodiment, said tablet contains said release-controlling excipient in an amount of from 1.0 mg to 3.0 mg.

In one embodiment, the sum of the weight of the release-controlling excipient and talc is from 1.5 mg to 3 mg, or from 1.8 mg to 2.4 mg, or from 2.0 mg to 2.2 mg.

In one embodiment, said tablet contains said active agent in an amount of from 2 to 3 mg.

In one embodiment, said tablet contains said release-controlling excipient in an amount of from 1.0 to 3.0 mg.

In one embodiment, the total weight of the tablet ranges from 4 to 10 mg.

The release-controlling excipient or mixture of excipients is selected in an amount sufficient to achieve the release characteristics described herein-below. Depending on its type, the typical content of the excipient is from about 10 wt.-% to about 80 wt.-% based on the total weight of the tablet.

In one embodiment, said tablet contains said active agent in an amount of from 2 to 3 mg, said release-controlling excipient in an amount of from 1.0 to 3.0 mg, wherein the total weight of the tablet ranges from 4 to 10 mg.

Modified Release Dosage Form Based on Granules and/or Pellets

In a further embodiment, the invention provides a modified release dosage form comprising at least one unit comprising neramexane, a pharmaceutically acceptable salt, solvate, conjugate, prodrug, polymorphic form, isomer, or derivative thereof, wherein said neramexane, a pharmaceutically acceptable salt, solvate, conjugate, prodrug, polymorphic form, isomer, or derivative thereof is embedded or dispersed in a solid matrix; and at least one release-controlling excipient; wherein said solid matrix is coated with said release-controlling excipient; wherein said unit is a granule or pellet; and wherein said unit has a diameter of from 0.1 to less than 6 mm.

The ingredients as described above in connection with the preparation of the solid matrix of the tablets may be used for the preparation of the granule(s) and pellet(s). Granules may be obtained in a granulation process, in which powder particles adhere to each other by different physical mechanisms. Processes such as thermoplastic granulation, aqueous or organic solvent based pot granulation, granulation in a tumbling mixer, granulation in a fluidized bed granulator, granulation by spray drying or dry granulation by compaction may be employed. A pellet may be produced by layering active material on a starter particle or by extrusion and spheronisation or by pelletizing in a fluidized bed or by thermal melting, forming, cooling processes.

For the coating of the granules or pellets with the release-controlling excipient, the methods and ingredients as described in connection with the coating of tablets may be used, e.g. a spraying method.

In one embodiment, said release-controlling excipient comprises talc or is employed in combination with talc or talcum powder.

In one embodiment, for preparation of the coating, said release-controlling excipient is mixed with talc or talcum powder. Subsequent to the mixing, the mixture may be applied according to the methods as described above such as spraying.

In one embodiment, the weight ratio of release-controlling agent to talc is from 1:1.5 to 1.5:1, or from 1.25:1 to 1:1.25 or is 1:1.

In one embodiment, said granule or pellet contains neramexane in an amount of from 2 to 3 mg.

In one embodiment, said granule or pellet contains said release-controlling excipient in an amount of from 1.0 mg to 3.0 mg.

In one embodiment, the sum of the weight of the release-controlling excipient and talc is from 1.5 mg to 3 mg, or from 1.8 mg to 2.4 mg, or from 2.0 mg to 2.2 mg.

Coating Thickness and Weight of Unit

In one embodiment, the coating thickness of the coating the units such as tablets, granules and/or pellets are coated with, is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

The coating thickness may be determined microscopically, e.g. via cross-sectioning a tablet. Such methods are known to a person skilled in the pharmaceutical formulation sciences.

In one embodiment, the unit, e.g. a tablet, granule or pellet, has a weight of from 0.1 to 100 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 0.1 to 20 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 1 to 15 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 2 to 10 mg, and the coating thickness ranges is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In one embodiment, the weight of the unit, e.g. a tablet, granule or pellet, has a weight of 0.1 to 100 mg, or 0.1 to 20 mg, or 1 to 15 mg, or 2 to 10 mg, and the coating thickness ranges from 1 to 500 µm, e.g. from 1 to 100 µm, or from 5 to 75 µm, or from 25 to 50 µm, or from 150 to 300 µm.

Third Aspect of the Invention
Modified Release Dosage Form, Wherein the Active Agent and the Release-Controlling Excipient are Embedded or Dispersed in a Solid Matrix According to a third aspect, the invention provides a modified release dosage form comprising at least one unit comprising a solid matrix comprising neramexane, a pharmaceutically acceptable salt, solvate, conjugate, prodrug, polymorphic form, isomer, or derivative thereof; and at least one release-controlling excipient; wherein said neramexane, a pharmaceutically acceptable salt, solvate, conjugate, prodrug, polymorphic form, isomer, or derivative thereof and said release-controlling excipient are embedded or dispersed in said solid matrix; wherein unit has a diameter of from 0.1 to less than 6 mm.

In one embodiment, the solid matrix is not coated with a release-controlling excipient.

In one embodiment, said solid matrix consists of or comprises said release-controlling excipient.

In one embodiment, the matrix comprises the release-controlling excipient in which said active agent is dispersed or embedded, or vice versa, or both the active agent and the release-controlling excipient are components of the matrix.

According to this third aspect, the invention provides at least one unit comprising a solid matrix comprising neramexane, a pharmaceutically acceptable salt, solvate, conjugate, prodrug, polymorphic form, isomer, or derivative thereof and at least one release-controlling excipient embedded or dispersed in said solid matrix; wherein said unit has a diameter of from 0.1 to less than 6 mm.

In one embodiment, said solid matrix consists of neramexane, a pharmaceutically acceptable salt, solvate, conjugate, prodrug, polymorphic form, isomer, or derivative thereof; and said release-controlling excipient is embedded or dispersed in said solid matrix. Synonymous to this embodiment is an embodiment, wherein said solid matrix consists of said release-controlling excipient; and said neramexane, a pharmaceutically acceptable salt, solvate, conjugate, prodrug, polymorphic form, isomer, or derivative thereof is embedded or dispersed in said solid matrix.

In one embodiment, said modified dosage form is a multiple unit dosage form.

In one embodiment, the unit is selected from tablets, granules and/or pellets, or a combination of two or three thereof.

According to one embodiment, the unit is a tablet. In one embodiment, said tablet is designed as a solid modified release matrix in which the active agent is embedded or dispersed, and from which it is released slowly over an extended period of time. Said decrease is controlled by said release-controlling excipient, which is already comprised in the matrix.

The release-controlling excipient or mixture of excipients is selected in an amount sufficient to achieve the release characteristics described herein-below. Depending on its type, the typical content of the excipient in the solid matrix is from about 10 wt.-% to about 80 wt.-% based on the total weight of the tablet.

Typically, the matrix does not disintegrate rapidly in aqueous media at physiological temperatures and pH values. Active compound release from the matrix may be controlled by the diffusion of the active compound through the matrix, by the erosion of the matrix, or both.

Depending upon the hydrophilic (erodable or non-erodable) or hydrophobic nature of the matrix, the matrix may be a material that swells upon contact with gastric fluid to a size that is large enough to promote retention in the stomach while the subject is in the digestive state. In addition to these diffusion based matrices, the matrix may also be in an erodable form. The digestive state is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. In other words, biological fluids migrate through the matrix and dissolve the active ingredient which is released by diffusion through the matrix which, simultaneously, modulates the release rate. The controlled-release matrix according to this aspect of the invention and the embodiments of this aspect is therefore selected as one that can swell to a size large enough to be retropelled and thereby retained in the stomach, causing the prolonged release of the drug to occur in the stomach rather than in the intestine.

In one embodiment, said release-controlling excipient is selected from the group consisting of water-insoluble lipids and waxes, water-insoluble polymers, and water-swellable polymers as defined above. If more than one release-controlling excipient is present in the matrix, it is also possible to combine excipients from different chemical sub-groups.

In one embodiment, the solid matrix is designed as a water-swellable, hydrophilic matrix comprising a release-controlling excipient selected from the group of water-swellable polymers. Suitable matrix-forming polymers may be water-soluble or water-insoluble. Suitable polymers absorb substantial amounts of water when placed into contact with aqueous media which typically results in the formation of an aqueous gel. The strength of the aqueous gel depends on the type and quantity of polymer and on the presence of other compounds in the matrix. Drug release may occur through diffusion of the active compound through aqueous micropores or microchannels within the three-dimensional polymeric gel network, and also through continuous erosion or disintegration of the most superficial gel layers of the matrix.

The polymers as defined in the section "General aspects of the invention" may be used such as cellulose polymers and their derivatives including, but not limited to, methylcellulose, ethylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, carboxymethyl ethylcellulose, cellulose acetate phthalate, polysaccharides and their derivatives, polyalkylene oxides, polyoxyethylenoxide polymers polyethylene glycols, chitosan, alginate, carrageen, galactomannan, tragacanth, agar, acacia, gellan, guar gum, gum arabicum, gum tragacanth, locust bean gum, xanthan gum, pectin, shellack, carboxymethyl amylopectin, chitosan, maleic anhydride copolymers, polyacrylate, polymethacrylate, methacrylate copolymer, polyvinyl alcohol, polyvinylpyrrolidone, polyvinylpyrrolidone-polyvinyl acetate copolymer and blends of polyvinylpyrrolidone and polyvinyl acetate, poly(2-ethyl-2-oxazoline), poly(ethyleneimine), polyurethane hydrogels, crosslinked polyacrylic acids and their derivatives, and mixtures of any of these.

Further examples are copolymers of the polymers listed above, including block copolymers and graft polymers, and lipids.

In one embodiment, said active substance is embedded in hydroxypropyl methylcellulose (HPMC), such as a hydroxypropyl methylcellulose as defined above.

It has been surprisingly found that hydroxypropyl methylcellulose is, even without the addition of another release-controlling excipient, capable of forming a swellable matrix from which a highly water-soluble form of neramexane, such as neramexane mesylate, is released over a prolonged period of time. This is in contrast to the common assumption that it is difficult to formulate modified release matrices with substantially water-soluble active agents based on one water-swellable polymer such as hydroxypropyl methylcellulose alone.

The hydroxypropyl methylcellulose grades as defined above may be used such as HPMC 2208, HPMC 2906 and HPMC 2910.

Polymers as defined above such as cellulose ethers such as ethylcellulose may also be used. Release-controlling excipients based on hydroxypropylcellulose, polyvinylpyrrolidone and/or polymethacrylate or polymethacrylate-copolymers are also suitable.

In one embodiment, the release-controlling excipient is based on a polyacrylate or a polymethacrylate or on polymethacrylate and/or polymethacrylate-copolymers, which optionally may contain ammonia acrylate moieties and/or ammonia methacrylate moieties. Suitable polymers are e.g. commercially available under the trademark Eudragit. Grades are e.g. Eudragit RS 30 D, Eudragit RL 30 D, Eudragit NE 30 D, Eudragit NE 40 D, Eudragit RS PO, or combinations of two or more thereof.

In another embodiment, said active substance is embedded in ethylcellulose. In one embodiment, a Surelease grade such as Surelease E-7-7050 is employed.

In another embodiment, said active substance is embedded in a cellulose acetate.

In one embodiment, one or two or more of the above mentioned polymers, i.e. polyacrylate and/or polymethacrylate; ethylcellulose; hydroxypropyl methylcellulose; polyvinyl acetate/polyvinyl pyrrolidone; cellulose acetate; may be used for the preparation of the matrix.

The relative amount of water-swellable polymer needed to achieve the desired release characteristics depends, inter alia, on the selected polymer type and grade, the presence or absence of other excipients having impact on drug release, and on the desired drug load of the matrix. The ratio of this polymer to the active compound is typically selected in the range from about 20:1 to about 1:20, or from about 15:1 to about 1:15, or from about 10:1 to about 1:10, and may be from about 5:1 to about 1:5. In one embodiment, the ratio of polymer to active compound is about 15:1 to about 13:1. In one embodiment, the ratio is 14:1 (weight/weight).

In one embodiment, the polymer is cellulose ether such as hydroxypropyl methylcellulose.

If a high-viscosity HPMC such as Methocel K 100M CR is chosen as principal release-controlling excipient, a typical ratio between the HPMC and the active compound is from about 4:1 to about 1:4 or from about 2:1 to about 1:2.

It has also been found to be useful to combine the drug substance and the water-swellable polymer with a further excipient selected from a class of dry binding agents or compression aids, which are also sometimes referred to as tabletting aids, fillers, diluents, or bulking agents. Such excipients are capable of increasing the internal binding forces of the matrix after compression. Usually they possess a high degree of plastic deformability. Their influence on drug dissolution or drug release may be relatively moderate. Examples of suitable members of this excipient category include anhydrous lactose, lactose monohydrate, calcium phosphate, dibasic calcium phosphate, calcium hydrogen phosphate, calcium sulfate, sucrose, dextrose, mannitol, sorbitol, cellulose, microcrystalline cellulose, and co-processed mixtures of lactose and microcrystalline cellulose (commercially available e.g. as Cellactose). A typical dry binding agent is microcrystalline cellulose, such as the commercially available Avicel PH.

Various types of microcrystalline cellulose are suitable for carrying out the invention. The product grades that are commercially available differ predominantly in particle size and moisture content, and should be selected depending on the method for the preparation of the matrix. For example, it has been found that Avicel PH 102 and certain other Avicel grades are particularly suitable for the preparation of a matrix tablet by direct compression or by a thermal or a melting process.

The content of the dry binding agent or compression aid in the dosage form of the invention is selected according to various formulation criteria, such as the type and grade of the dry binding agent or compression aid, the type, grade, and quantity of the water-swellable polymer, the active compound load, the presence of further excipients having an impact on compressibility etc. Typically, the content is at least about 10 wt.-% relative to the weight of the matrix, and often at least about 15 wt.-%. In further embodiments, the content is between about 15 wt.-% and about 60 wt.-%, such as between about 15 wt.-% and about 50 wt.-%.

The ratio of the water-swellable and/or porous polymer and the dry binding agent or compression aid in the matrix is typically in the range from about 10:1 to 1:20, such as 6:1 to 1:6, such as from about 5:1 to 1:5, and in particular embodiments from about 3:1 to about 1:3, and from about 2:1 to 1:2, respectively. In another embodiment, the water-swellable polymer is hydroxypropyl methylcellulose, in particular Methocel K 100M CR, and the dry binding agent or compression aid is microcrystalline cellulose, and they are present in the matrix in a ratio from about 2:1 to about 1:2, and at a total content of both excipients in the matrix from about 50 wt.-% to about 85 wt.-%, such as between about 60 wt.-% and about 75 wt.-%.

As indicated above, it is an embodiment of the dosage form, specifically the tablet, that it is designed as a matrix, e.g. a compressed or a non compressed matrix tablet.

Various methods are available and suitable for the preparation of such tablets. One typical method is the compression of granules prepared by wet or dry granulation, and the direct compression of powder mixtures into compacts, or a thermal or melting process.

Wet-granulation and dry granulation methods involve the methods as referred to in the section "Second aspect of the invention".

Direct compression involves the compaction of powder mixtures into tablets without prior granulation. This method is potentially cost-effective as it avoids the sequence of process steps involved in the preparation of granules, and it is also suitable for the processing of sensitive active compounds. The presence of a dry binding agent or compression aid in the formulation is usually required or desirable for achieving useful tablet strengths. However, direct compression may not always be possible. For example, certain powder mixtures do not exhibit a sufficient product flow on tablet presses or do not yield suitable tablet physical characteristics, so that in these cases the use of granulation is preferred.

It has been found that powder mixtures of a water-swellable polymer, a dry binding agent or compression aid, and a water-soluble salt of neramexane and, optionally, further excipients, are suitable for direct compression. Typically, the three components (i.e. water-swellable polymer, dry binding agent, and neramexane salt) represent at least about 75 wt.-% of the powder mixture, and the optional further excipients represent no more than about 25 wt.-%. In another embodiment, the water-swellable polymer (or mixture of water-swellable polymers), the dry binding agent or compression aid (or mixture of more than one member of this class), and the active compound together represent at least about 85 wt.-% of the matrix formulation, such as from about 85 wt.-% to about 99.9 wt.-%, or from about 90 wt.-% to about 99.5 wt.-%. In a further embodiment, they constitute from about 95 wt.-% to about 99 wt.-% of the matrix.

According to another embodiment, the invention involves the direct compression of a powder mixture comprising hydroxypropyl methylcellulose, such as Methocel K 100M CR, microcrystalline cellulose, such as Avicel PH 102, and neramexane such as neramexane mesylate. Typically, each of these three components represents from about 10 wt.-% to about 50 wt.-% of the powder that is compacted to form the matrix. In another embodiment, the ratio of neramexane mesylate to the other two components together is from about 1:1 to about 1:5, and more preferably from about 1:1 to about 1:3, such as about 1:2.

The powder mixture may comprise one or more further excipients. Among the further excipients are members of the classes of lubricants, such as magnesium stearate, stearic acid, calcium stearate, sodium stearyl fumarate, mineral oil, hydrogenated vegetable oil, and polyethylene glycol; and glidants, such as colloidal silicon dioxide, starch, calcium or magnesium stearate, and talc.

The lubricant is typically used at a level from about 0.1 wt. % to about 2 wt.-%, relative to the weight of the matrix. A representative lubricant is magnesium stearate, which also has some glidant properties. If magnesium stearate is selected, a useful content range is from about 0.2 wt.-% to about 1.5 wt.-%, in particular from about 0.25 wt.-% to about 1 wt.-%.

Similarly, the amount of glidant should be selected at a relatively low level, such as below about 5 wt.-%. Among the representative glidants are colloidal silicon dioxide and talc. If one or both of these glidants are incorporated, the glidant content in the matrix is typically in the region from about 0.25 wt.-% to about 2.5 wt.-%, or from about 0.5 wt.-% to about 1.5 wt.-%.

Such matrix dosage forms have been surprisingly found to exhibit favorable tablet properties. For example, it was found that the release profile of the active compound was relatively independent of the compression force, at least over a broad range of practically useful compression forces. Mixtures of Methocel K 100M CR, Avicel PH 102, neramexane mesylate, magnesium stearate and colloidal silicon could be tabletted on a standard rotary tablet press using main compression forces ranging from about 2 kN to about 21 kN. The resulting tablets varied substantially in their tensile strength, from about 10 N to about 100 N, with higher compression forces leading to harder tablets. However, the dissolution profiles of these tablets were substantially similar, even when the hardest tablets were compared to the softest tablets with identical composition, indicating a remarkably robust formulation. In particular, it was found that within the hardness range from about 20 N to about 80 N, the dissolution profiles are substantially independent of the hardness or tensile strength of the tablets. The tensile strength may vary from about 30 N to about 500 N, such as from about 40 N to about 300 N or from about 50 N to about 200 N. Moreover, the tensile strength of the film-coated tablets may be above 120 N.

In other embodiments, the tablets are produced according to methods which do not require a compression step. Suitable methods such as thermal processes and melt processes are known in the art.

Taste Masking Coating of the Solid Matrix

According to a further embodiment, the dosage form, specifically the tablet, of the present invention is designed as a compressed or non-compressed matrix comprising the active agent and the release-controlling excipient, which is coated with a coating. In one embodiment, the coating does not comprise a release-controlling excipient.

In one embodiment, such coating is a sugar or a polymeric coating, to provide taste masking of an active compound which typically has a poor taste.

Typically, the coating of the matrix is a polymeric film coating. Film compositions suitable for taste masking are widely known in the field of pharmaceuticals, and they may be based on various types of polymers. Typically, a taste masking coating prevents the direct contact of the active compound with saliva during administration, and rapidly dissolves or disintegrates after the dosage form has been swallowed.

Suitable polymers for such coatings include e.g. cationic methacrylate copolymers, such as dimethylaminoethyl methacrylate-methylmethacrylate copolymer (DMA-MMA), which is insoluble in aqueous media above pH 5 (such as saliva), but dissolves in acidic media (such as gastric fluid). Other potentially suitable polymers include hydroxypropyl cellulose, hydroxypropyl methylcellulose, hydroxyethyl methylcellulose, methacrylic acid copolymers other than DMA-MMA, polyvinyl alcohol-polyethylene glycol copolymer, ethyl acrylate-methyl methacrylate copolymer, polyvinyl alcohol, carrageenan, and mixtures thereof.

The coating composition may comprise further excipients to improve the properties of the coating or its processibility, such as one or more excipients selected from the classes of plasticizers, stabilizers, pigments, coloring agents, dispersing agents, surfactants, sugars, fillers, anti-adhesives, water vapor permeability-modifying agents etc. Commercially available coating compositions often represent pre-mixes of one or more film-forming polymers and at least one further excipient. Useful commercial coating compositions include the water-soluble grades of Sepifilm, such as Sepifilm 002, Sepifilm 003, Sepifilm 752, Sepifilm LP grades including Sepifilm LP 770; water-soluble grades of Kollicoat, such as Kollicoat IR and Kollicoat Protect; furthermore Opadry, virtually all grades of Instacoat, LustreClear, and similar products.

The taste masking coating may have other functions. For example, the coating potentially improves the mechanical and even the chemical stability of the matrix tablet, and it may also improve the appearance of the tablet, its appeal to the patient, swallowability and other features.

The coatings may be applied to the matrix by any conventional technique and equipment, such as by pan coating or fluid-bed coating. Typically, an aqueous, hydroalcoholic, or organic liquid comprising the dispersed or dissolved film-forming polymer(s) and any optional further excipients is atomized and deposited on pre-formed tablet cores which have optionally been de-dusted, under a continuous flow of warm air to dry the coating composition on the tablet cores.

In one embodiment, the invention relates to a modified release dosage form such as a modified multiple unit dosage form, wherein the unit is a tablet, comprising neramexane mesylate and as release-controlling excipient a polyvinylpyrrolidone or a blend of a polyvinylpyrrolidone and polyvinyl acetate, or a hydroxypropyl methylcellulose, wherein said mesylate and said polyvinylpyrrolidone, or a polyvinylpyrrolidone and polyvinyl acetate blend, or hydroxypropyl methylcellulose, embedded or dispersed in a solid matrix, wherein said tablet has a diameter of from 1.5 to 3.5 mm.

In one embodiment, said tablet contains said active agent in an amount of from 0.5 to 3 mg.

In one embodiment, said tablet contains said release-controlling excipient in an amount of from 4.0 to 15.0 mg.

In one embodiment, the total weight of the tablet ranges from 5 to 20 mg.

In one embodiment, said tablet contains said active agent in an amount of from 1.5 to 3.5 mg, said release-controlling excipient in an amount of from 4.0 to 15.0 mg, wherein the total weight of the tablet ranges from 5 to 20 mg.

Fourth Aspect of the Invention
Modified Release Dosage Form, Wherein the Active Agent and the Release-Controlling Excipient are Embedded or Dispersed in a Solid Matrix; and the Solid Matrix is Coated with a Release-Controlling Excipient According to a fourth aspect, the invention provides a modified release dosage form which is a combination of the modified release dosage form according to the second and third aspect of the invention. The methods and release-controlling excipients disclosed therein may be used for the preparation of respective formulations of a modified release dosage form.

Thus, according to this aspect, the invention provides a modified release dosage form comprising at least one unit comprising a solid matrix comprising neramexane, a pharmaceutically acceptable salt, solvate, conjugate, prodrug, polymorphic form, isomer, or derivative thereof and at least one release-controlling excipient embedded or dispersed in said solid matrix; wherein said solid matrix is coated with a release-controlling excipient; wherein said release-controlling excipients may be the same excipients or may be different from each other; and wherein said unit has a diameter of from 0.1 to less than 6 mm.

According to this fourth aspect, the invention provides at least one unit comprising a solid matrix comprising neramexane, a pharmaceutically acceptable salt, solvate, conjugate, prodrug, polymorphic form, isomer, or derivative thereof and at least one release-controlling excipient embedded or dispersed in said solid matrix; wherein said solid matrix is coated with a release-controlling excipient; wherein said release-controlling excipients may be the same excipients or may be different from each other; and wherein said unit has a diameter of from 0.1 to less than 6 mm.

In one embodiment, said solid matrix consists of neramexane, a pharmaceutically acceptable salt, solvate, conjugate, prodrug, polymorphic form, isomer, or derivative thereof; and said release-controlling excipient is embedded or dispersed in said solid matrix. Synonymous to this embodiment is an embodiment, wherein said solid matrix consists of a release-controlling excipient; and said neramexane, a pharmaceutically acceptable salt, solvate, conjugate, prodrug, polymorphic form, isomer, or derivative thereof is embedded or dispersed in said solid matrix.

In one embodiment, the release-controlling excipient in the solid matrix is identical to the release-controlling excipient the solid matrix is coated with.

In another embodiment, the release-controlling excipient in the solid matrix is different from the release-controlling excipient the solid matrix is coated with.

In one embodiment, said matrix comprises a pharmaceutical composition comprising said active agent. In one embodiment, said pharmaceutical composition comprises or consists of said active agent and one or more of the excipients as described above.

In one embodiment, the release-controlling excipient in the solid matrix and/or in the coating comprises talc or is employed in combination with talc or talcum powder.

In one embodiment, said modified dosage form is a multiple unit dosage form.

In one embodiment, the unit is selected from tablets, granules and/or pellets, or a combination of two or three thereof.

Coating Thickness and Weight of Unit

In one embodiment, the coating thickness of the coating the units such as tablets, granules and/or pellets are coated with, is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

The coating thickness may be determined microscopically, e.g. via cross-sectioning a tablet. Such methods are known to a person skilled in the pharmaceutical formulation sciences.

In one embodiment, the unit, e.g. a tablet, granule or pellet, has a weight of from 0.1 to 100 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 0.1 to 20 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 1 to 15 mg, and the coating thickness ranges from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In another embodiment, the unit, e.g. a tablet, granule or pellet, has a weight of from 2 to 10 mg, and the coating thickness ranges is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In one embodiment, the weight of the unit, e.g. a tablet, granule or pellet, has a weight of 0.1 to 100 mg, or 0.1 to 20 mg, or 1 to 15 mg, or 2 to 10 mg, and the coating thickness ranges from 1 to 500 µm, e.g. from 1 to 100 µm, or from 5 to 75 µm, or from 25 to 50 µm, or from 150 to 300 µm.

Fifth Aspect of the Invention

Modified Release Dosage Form, Wherein the Active Agent is Deposited on a Solid Matrix and the Solid Matrix Comprising Said Deposited Active Agent is Coated with a Release-Controlling Excipient According to a fifth aspect, the invention provides a modified release dosage form comprising at least one unit comprising a solid matrix comprising neramexane, a pharmaceutically acceptable salt, solvate, conjugate, prodrug, polymorphic form, isomer, or derivative thereof deposited on said solid matrix; and at least one release-controlling excipient; wherein said solid matrix comprising said deposited neramexane, a pharmaceutically acceptable salt, solvate, conjugate, prodrug, polymorphic form, isomer, or derivative thereof is coated with said release-controlling excipient; wherein said unit has a diameter of from 0.1 to less than 6 mm.

According to this fifth aspect, at least one unit is provided comprising a solid matrix comprising neramexane, a pharmaceutically acceptable salt, solvate, conjugate, prodrug, polymorphic form, isomer, or derivative thereof deposited on said solid matrix; and at least one release-controlling excipient; wherein said solid matrix comprising said deposited neramexane, a pharmaceutically acceptable salt, solvate, conjugate, prodrug, polymorphic form, isomer, or derivative is coated with said release-controlling excipient; wherein said unit has a diameter of from 0.1 to less than 6 mm.

In one embodiment, said modified dosage form is a multiple unit dosage form.

In one embodiment, said solid matrix consists of or comprises said release-controlling excipient.

In one embodiment, the solid matrix are particles of sugars such as sucrose, mannitol; polymers such as solid polyethylenglycol, hydroxypropyl cellulose, hydroxypropyl methyl cellulose; inorganic substances such as calcium phosphate, talc, fumed silica.

In one embodiment, the solid matrix is made of sugar spheres, microcrystalline cellulose, or hydrated sugars such as mannitol or sorbitol.

In one embodiment, the solid matrix is selected from a polysaccharide such as a starch or a combination of starch and sugar such as a saccharose.

In one embodiment, said polysaccharide is saccharose commonly known as sugar. In one embodiment, said polysaccharide is crystallized.

In one embodiment, the active agent may be provided as organic solutions or aqueous dispersions and sprayed onto said matrix using conventional coating equipment. Typically, the solution or dispersion will also contain excipients such as binders. Suitable binders are e.g. commercially available grades such as Klucel or Opadry grades.

Subsequently, said matrix comprising said active agent deposited thereon may be coated with said release-controlling excipient in a method as referred to in e.g. section "General aspects of the invention".

In one embodiment, release-controlling excipients based on polymethacrylate and/or polymethacrylate-copolymers such as Eudragit RS 30 D, Eudragit RL 30 D, Eudragit RS PO, Eudragit NE 30 D and Eudragit NE 40 D, or a combination of two or more thereof are employed.

In one embodiment, said release-controlling excipient comprises talc or is employed in combination with talc or talcum powder.

In one embodiment, for preparation of the coating, said release-controlling excipient is mixed with talc or talcum powder. Subsequent to the mixing, the mixture may be applied according to the methods as described above such as spraying.

In one embodiment, the invention relates to a modified release dosage form comprising at least one unit comprising neramexane mesylate, and at least one release-controlling excipient based on polyacrylate or a polymethacrylate or a polyacrylate copolymer and/or polymethacrylate copolymer, which optionally may contain ammonia acrylate moieties and/or ammonia methacrylate moieties, wherein said unit is sugar or starch, and wherein said active agent is deposited on sugar crystals or on starch as solid matrix; wherein said solid matrix comprising said active agent deposited thereon is coated with said release-controlling excipient; wherein said unit has a diameter of from 0.3 to 1.0 mm.

In one embodiment, said unit contains said active agent in an amount of from 0.1 to 3 mg.

In one embodiment, said unit contains said release-controlling excipient in an amount of from 0.1 to 3.0 mg.

In another embodiment, the total weight of the unit ranges from 1 to 8 mg.

In one embodiment, In one embodiment, said unit contains said active agent in an amount of from 0.1 to 3 mg, said release-controlling excipient in an amount of from 0.1 to 3.0 mg, wherein the total weight of the unit ranges from 1 to 8 mg.

In one embodiment, the coating thickness of the coating the units are coated with, is from 1 to 500 µm, e.g. from 1 to 100 µm, or from 5 to 75 µm, or from 25 to 50 µm, or from 50 to 500 µm, or from 75 to 400 µm, or from 100 to 350 µm, or from 150 to 300 µm.

In one embodiment, the invention provides a release dosage form comprising at least one unit comprising a pharmaceutical composition comprising as an active agent neramexane, a pharmaceutically acceptable salt, solvate, conjugate, prodrug, polymorphic form, isomer, or derivative thereof, and a release-controlling excipient, wherein said unit has a diameter of from 0.1 to less than 6 mm, and wherein said active agent is not deposited on a solid matrix, and wherein said solid matrix comprising said deposited active agent is not coated with said release-controlling excipient.

In one embodiment according to the first, second, third, fourth and fifth aspect, said release-controlling excipient is selected from a polyacrylate and/or a polymethacrylate, optionally comprising ammonia acrylate moieties and/or ammonia methacrylate moieties; or from a physical mixture of polyvinyl acetate and polyvinylpyrrolidone; or from a hydroxypropyl methylcellulose; or from a mixture of two or more thereof. The active agent is neramexane, a pharmaceutically acceptable salt such as the mesylate, solvate, conjugate, prodrug, polymorphic form, isomer, or derivative thereof. In one embodiment, the active agent is neramexane mesylate.

Sixth Aspect of the Invention

According to a sixth aspect, the invention provides a modified release dosage form which comprises at least one unit as described above.

In one embodiment, said modified release dosage form is a multiple unit dosage form.

In a further aspect, the invention provides a tablet comprising at least two units according to the invention, wherein said unit is a granule and/or a pellet. The tablet may be manufactured from granules and/or pellets according to the methods referred to in the section "Definition of terms", e.g. by compression or thermal or melting processes.

In one embodiment, the at least one unit according to the invention, or the modified release dosage form according to the invention, or the tablet according to the invention comprising at least two units according to the invention may be packaged.

In one embodiment, the unit according to the invention, or the modified release dosage form according to the invention, or at least one tablet according to the invention comprising at least two units according to the invention may be packaged in a capsule or stickpack.

Accordingly, the invention provides a capsule comprising at least one unit according to the invention, or the modified release dosage form according to the invention, or at least one tablet according to the invention comprising at least two units according to the invention, or a stickpack comprising at least one unit according to the invention, or the release dosage form according to the invention or at least one tablet according to the invention comprising at least two units according to the invention.

In one embodiment, said capsule or stickpack comprises at least one unit or the multiple unit dosage form according to the invention or at least one tablet according to the invention comprising at least two units according to the invention.

In one embodiment, said multiple unit dosage form is encapsulated by said capsule.

Capsules having encased or encapsulated pharmaceutically active ingredients therein are known in the art.

In one embodiment, said capsule is a hard-shelled capsule as known in the art.

In one embodiment, said capsule is made from gelatine or from plant-based gelling substances such as carrageenans or cellulose and derivatives or starch derivatives and modified forms of starch and cellulose.

In one embodiment, the capsules are made in two parts as known in the art. Before use, the two halves are separated, the capsule is filled with the multiple unit dosage form according to the invention such as tablets, granules or pellets, by filling one half of the capsule with the same, and the other half of the capsule is pressed on.

In one embodiment, the capsule is filled with one or preferably more than one unit of the release dosage form according to the invention. The number of units depends on the quantity of active agent (ingredient) contained therein, and on factors such as the specific condition which is to be treated, the weight of the patient, the patient's condition, the dosing regimen etc.

It is currently believed that a cumulated daily oral dose of approx. 5 to about 150 mg, such as from about 5 mg to about 120 mg or from approx. 5 mg to 100 mg of neramexane or of a salt of neramexane such as neramexane mesylate, is therapeutically effective for the treatment of at least some of the conditions for which neramexane appears to be useful. A cumulated daily oral dose of about 10 mg to about 90 mg of neramexane or of a salt of neramexane such as neramexane mesylate may be further useful.

Moreover, a cumulated daily dose of about 25 mg to about 100 mg, such as 62.5 mg, 75 mg, 87.5 mg, and 100 mg of neramexane mesylate or an equimolar amount of neramexane, another pharmaceutically acceptable salt, a solvate, an isomer, a conjugate, a prodrug or a derivative thereof, such as neramexane hydrochloride, is therapeutically effective and simultaneously avoids excessive side effects. Furthermore, a cumulated daily dose of about 40 mg to about 80 mg or of about 50 mg to about 75 mg of neramexane mesylate or an equimolar amount of neramexane, another pharmaceutically acceptable salt, a solvate, an isomer, a conjugate, a prodrug, a polymorphic form, or a derivative thereof may also be useful.

The capsule allows to deliver the release dosage form such as a multiple unit dosage form according to the invention to the GI tract. After the deterioration of the shell of the capsule, the units release the active agent as explained below.

In an alternative embodiment, the release dosage form according to the invention such as a multiple unit dosage form is encapsulated in a stickpack.

Stickpacks are known in the art for packaging e.g. dietary supplements or medicaments in the form of powders or beads or the like.

For administration of the release dosage form, the stickpack is opened and the content thereof is swallowed.

Seventh Aspect of the Invention

According to a seventh aspect, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; and in which the release profile may be further adjusted to a predetermined or tailor-made dissolution profile.

In one embodiment, such predetermined or tailor-made dissolution profile may be provided by employing an at least one release-controlling excipient comprising at least one first and at least one second release-controlling excipient, wherein the at least one first and the at least one second release-controlling excipient are different from one another.

In one embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; and wherein said at least one release-controlling excipient comprises at least one first and at least one second release-controlling excipient, wherein the at least one first and the at least one second release-controlling excipient are different from one another.

In one embodiment, the unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; comprises said at least one release-controlling excipient in a coating, wherein said at least one release-controlling excipient and therefore the coating comprises at least one first and at least one second release-controlling excipient, wherein the at least one first and the at least one second release-controlling excipient are different from one another.

More specifically, in one embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; and wherein said at least one release-controlling excipient used for the coating of the unit according to the first, the second, the fourth and/or the fifth aspect of the invention, comprises at least one first and at least one second release-controlling excipient, wherein the at least one first and the at least one second release-controlling excipient are different from one another.

In one embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; wherein said unit comprises a solid matrix consisting of neramexane, a pharmaceutically acceptable salt, solvate, conjugate, prodrug, polymorphic form, isomer, or derivative thereof; wherein said solid matrix is coated with said at least one release-controlling excipient; wherein said at least one release-controlling excipient used for said coating comprises at least one first and at least one second release-controlling excipient, wherein the at least one first and the at least one second release-controlling excipient are different from one another.

In another embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; wherein the unit comprises a solid matrix comprising neramexane, a pharmaceutically acceptable salt, solvate, conjugate, prodrug, polymorphic form, isomer, or derivative thereof; wherein said solid matrix is coated with said at least one release-controlling excipient; wherein said at least one release-controlling excipient used for said coating comprises at least one first and at least one second release-controlling excipient, which are different from one another.

In a further embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; wherein said unit comprises a solid matrix comprising neramexane, a pharmaceutically acceptable salt, solvate, conjugate, prodrug, polymorphic form, isomer, or derivative thereof embedded or dispersed in said at least one release-controlling excipient; wherein said solid matrix is coated with at least one further release-controlling excipient; wherein said release-controlling excipients may be the same excipients or may be different from each other; wherein the at least one release-controlling excipient used for said coating comprises at least one first and at least one second release-controlling excipient, which are different from one another.

In still another embodiment, the invention relates to a unit comprising neramexane, a pharmaceutically acceptable salt, solvate, conjugate, prodrug, polymorphic form, isomer, or derivative thereof; and at least one release-controlling excipient; wherein said unit has a diameter of from 0.1 to less than 6 mm; wherein said unit comprises a solid matrix comprising neramexane, a pharmaceutically acceptable salt, solvate, conjugate, prodrug, polymorphic form, isomer, or derivative thereof deposited on said solid matrix; wherein said solid matrix comprising said deposited neramexane, a pharmaceutically acceptable salt, solvate, conjugate, prodrug, polymorphic form, isomer or derivative is coated with said at least one release-controlling excipient; wherein said at least one release-controlling excipient used for said coating comprises at least one first and at least one second release-controlling excipient, which are different from one another.

The term " . . . which are different from one another" means that the at least one first and the at least one second release-controlling excipient differ from one another with respect to the chemical composition thereof. In another embodiment, the term " . . . which are different from one another" means that the at least one first and the at least one second release-controlling excipient differ from one another with respect to the physical properties. In still another embodiment, the term " . . . which are different from one another" means that the at least one first and the at least one second release-controlling excipient do not only differ from one another with respect to the chemical composition thereof, but also with respect to the physical properties.

In one embodiment, the at least one first and the at least one second release-controlling excipient are selected from excipients as defined in the section "Summary of the Invention".

In one embodiment, the weight ratio of the at least one first release-controlling excipient to the at least one second release-controlling excipient is in the range of from 20:1 to 1:1.

In another embodiment, the ratio is in the range of from 15:1 to 2:1.

In one embodiment, the weight expressed in weight-% of the at least one first release-controlling excipient and the at least one second release-controlling excipient ranges from 2 to 25% based on the total weight of the unit. In another embodiment, the weight expressed in weight-% of the at least one first release-controlling excipient and the at least one second release-controlling excipient ranges from 5 to 25% or 5 to 20% based on the total weight of the unit.

In another embodiment, the weight of the at least one first release-controlling excipient and the at least one second release-controlling excipient ranges from 5 to 25% based on the total weight of the unit; and the weight ratio of the at least one first release-controlling excipient to the at least one second release-controlling excipient is in the range of from 20:1 to 1:1 or of from 15:1 to 2:1.

In one embodiment, the at least one first and the at least one second release-controlling excipient are used for said coating, e.g. are applied to said solid matrix, in the form of a mixture comprising said at least one first and said at least one second release-controlling excipients.

In another embodiment, the at least one first and the at least one second release-controlling excipient are used for said coating in a form separated from one another, but are simultaneously used for said coating.

In another embodiment, said at least one first and said at least one second release-controlling excipient are used for said coating, e.g. are applied to said solid matrix, consecutively.

The at least one first and the at least one second release-controlling excipient may be applied to the solid matrix according to known methods, e.g. by a spraying technique. The methods as disclosed e.g. in the section "First aspect of the invention" may be employed.

In one embodiment, the coating further comprises a sub-coating, an anti-sticking agent, a plasticizer, a glidant, a lubricant and/or a stabilizer.

The term "sub-coating" means that prior to the coating of the solid matrix with the at least one release-controlling excipient comprising the at least one first and the at least one second release-controlling excipient, the solid matrix is coated. In one embodiment, the coating may comprise or consist of a release-controlling excipient as defined in the section "Summary of the Invention". In another embodiment, the sub-coating may comprise or may consist of any polymer which is capable of forming a coating.

Suitable anti-sticking agents are known in the field of preparing e.g. tablets. In one embodiment, talc may be employed as a suitable anti-sticking agent.

A glidant is e.g. silica or talc.

A lubricant is e.g. magnesium stearate.

A stabilizer may be used in order to improve the compatibility of the ingredients forming the coating comprising the at least first and the at least second release-controlling excipient. Suitable stabilizers are known in the field of preparing e.g. tablets. In one embodiment, a polysorbate may be employed as stabilizer.

Suitable plasticizers are known in the field of preparing e.g. tablets. In one embodiment, an ester of citric acid such as triethyl citrate may be employed. In other embodiments, the plasticizers as e.g. disclosed in the section "First aspect of the invention" may be employed.

In one embodiment, the coating thickness and the weight of the units corresponds to the coating thickness and weight as disclosed in the section "First aspect of the invention"

Specific Embodiments

In one embodiment, said at least one first release-controlling excipient and said at least one second release-controlling excipient are polymers selected from a polyacrylate and/or a polymethacrylate (poly(meth)acrylate).

The term "polyacrylate and/or polymethacrylate (poly (meth)acrylate)" is not restricted to a polymer which consists of polyacrylate or polymethacrylate moieties, or which consists of polyacrylate and polymethacrylate moieties, but rather encompasses any polymer which contains or comprises polyacrylate or polymethacrylate moieties. Accordingly, the term encompasses e.g. copolymers of poly(meth) acrylate. The carboxylic group within the polymer may be present as carboxylic group as such, as ester group or as carboxylate group, wherein the counterion preferably is selected from an ammonium ion.

In one embodiment, the term encompasses copolymers of acrylic and methacrylic acids, i.e. the polymer consists of polyacrylate and polymethacrylate moieties.

In one embodiment, said poly(meth)acrylate is a ionic poly(meth)acrylate.

In one embodiment, the first and the second release-controlling excipient are selected from ionic poly(meth)acrylates, wherein the poly(meth)acrylates are different from one another. In one embodiment, the poly(meth)acrylates differ from one another with respect to the amount of ionic groups.

In one embodiment, the ionic poly(meth)acrylate comprises carboxylate groups. In another embodiment, the ionic poly(meth)acrylate comprises carboxylate groups and ions selected from sodium, potassium, or ammonium.

In one embodiment, said ionic poly(meth)acrylate comprises ammonium(meth)acrylate moieties.

The term "ammonium ion" encompasses protonated ammonia and protonated primary, secondary, or tertiary amines as well as the cations of quaternary nitrogen bases.

Ionic poly(meth)acrylates such as ionic poly(meth)acrylates comprising ammonia or ammonium ions are known in the art and/or may be prepared according to known methods. E.g., Eudragit® RS 30D or Eudragit® RL 30D are commercially available products.

In one embodiment, a coating comprising different ionic poly(meth)acrylates such as poly(meth)acrylates comprising ammonium(meth)acrylate moieties as first and second release-controlling excipients (such as Eudragit® RS 30D and Eudragit® RL 30D) provides for a "pulsatile release profile".

In another embodiment, said at least one first release-controlling excipient is a polymer selected from polyacrylate or polymethacrylate or ethylcellulose; or is a mixture of two or more thereof.

The term "ethylcellulose" is not restricted to a polymer which consists of ethylcellulose moieties, but rather encompasses any polymer which contains or comprises ethylcellulose moieties.

In one embodiment, said at least one first release-controlling excipient is a polymer selected from polyacrylate or polymethacrylate or ethylcellulose; or is a mixture of two or more thereof; and the at least one second release-controlling excipient is a polymer selected from methylcellulose, hydroxymethylcellulose, hydroxyethylcellulose, hydroxypropylcellulose, hydroxybutylcellulose, hydroxyethyl methylcellulose, hydroxypropyl methylcellulose, carboxymethylcellulose, carboxymethyl ethylcellulose, polysaccharides and their derivatives, cellulose acetate phthalate, polyalkylene oxides, polyoxyethylenoxide polymers, polyethylene glycols, chitosan, alginate, carrageen, galactomannan, tragacanth, agar, acacia, gellan, guar gum, gum arabicum, gum tragacanth, locust bean gum, xanthan gum, pectin, shellack, carboxymethyl amylopectin, chitosan, maleic anhydride copolymers, polyvinyl alcohol, polyvinylpyrrolidone, polyvinylpyrrolidone-polyvinyl acetate copolymer and blends of polyvinylpyrrolidone and polyvinyl acetate, poly (2-ethyl-2-oxazoline), poly(ethyleneimine), polyurethane hydrogels, crosslinked polyacrylic acids and their derivatives; copolymers of the aforementioned polymers including block copolymers and graft polymers; lipids and waxes including, for example, beeswax, natural or synthetic mono-, di- and triglycerides of medium and long chain fatty acids such as hydrogenated vegetable oils, carnauba wax, petroleum wax, microcrystalline wax, long chain fatty acids, long chain fatty alcohols, esters of fatty acids and fatty alcohols; and mixtures of any of these compounds.

In one embodiment, said poly(meth)acrylate is a non-ionic poly(meth)acrylate.

In one embodiment, said non-ionic poly(meth)acrylate is an ester of poly(meth)acrylate.

Non-ionic poly(meth)acrylates such as non-ionic polymethacrylates are known in the art and/or may be prepared according to known methods. E.g., Eudragit® NE 30D is a commercially available product.

In one embodiment, said at least one second release-controlling excipient is a hydroxypropylmethylcellulose, or is a polyvinyl alcohol, or is a polyvinyl acetate.

The term "polyvinyl alcohol" is not restricted to a polymer which comprises moieties of polyvinyl alcohol only, but rather encompasses any polymer containing or comprising moieties of polyvinyl alcohol such as grafted polyvinyl alcohol. A grafted polyvinyl alcohol is e.g. a polyvinyl alcohol grafted with a polyethylene glycol.

The term "polyvinyl acetate" is not restricted to a polymer which comprises moieties of polyvinyl acetate only, but rather encompasses any polymer containing or comprising moieties of polyvinyl acetate.

In one embodiment, the at least one first release-controlling excipient is a polymer selected from a non-ionic poly(meth) acrylate such as a poly(meth)acrylate comprising ester groups; and the at least one second release-controlling excipient is a polymer selected from a hydroxypropylmethylcellulose.

In one embodiment, such combination of a non-ionic poly (meth)acrylate such as an esterified poly(meth)acrylate and hydroxypropylmethylcellulose as first and second release-controlling excipient provides for a release profile which may be characterized by a "flat sigmoidal shape" or a "flat linear shape".

In still another embodiment, the at least one first release-controlling excipient is a polymer selected from an ethylcellulose; and the at least one second release-controlling excipient is a polymer selected from a polyvinyl alcohol such as a grafted polyvinyl alcohol, or is a polyvinyl acetate. A grafted polyvinyl alcohol is e.g. a polyvinyl alcohol grafted with a polyethylene glycol. With this embodiment, it is possible to further extend the overall retardation period, i.e. to minimize the amount of released active agent and to extend the release period.

In one embodiment, the unit according to the invention comprises a solid matrix comprising neramexane, a pharmaceutically acceptable salt, solvate, conjugate, prodrug, polymorphic form, isomer, or derivative thereof embedded or dispersed in said solid matrix; wherein said solid matrix is coated with said at least one release-controlling excipient;

wherein said at least one release-controlling excipient used for said coating comprises at least one first and at least one second release-controlling excipient, which are different from one another; wherein said at least one first release-controlling excipient and said at least one second release-controlling excipient are polymers selected from ionic polyacrylate and/or polymethacrylate; and wherein the weight of the solid matrix expressed in weight % is in the range of from 80 to 90%, the weight of the first release controlling excipient is in the range of from 7 to 18%, and the weight of the second release controlling excipient is in the range of from 0.1 to 11%, wherein the sum of the weights of the solid matrix and the first and the second release-controlling excipient equals 100%.

In one embodiment, the weight of the solid matrix is in the range of from 81 to 88%, the weight of the first release controlling excipient is in the range of from 8 to 17%, and the weight of the second release controlling excipient is in the range of from 0.5 to 10%.

In one embodiment, the coating further comprises a plasticizer such as triethylcitrate; a stabilizer such as polysorbate; and/or an antisticking agent such as talc.

In one embodiment, the weight of neramexane, a pharmaceutically acceptable salt, solvate, conjugate, prodrug, polymorphic form, isomer, or derivative thereof embedded or dispersed in said solid matrix, ranges from 30 to 60 weight % or from 35 to 45 weight % based on the total weight of the solid matrix.

In one embodiment, the solid matrix further comprises a binder such as microcrystalline cellulose; a glidant such as silica and/or talc; a lubricant such as magnesium stearate.

In one embodiment, said at least one first release-controlling excipient and said at least one second release-controlling excipient are polymers selected from ionic polyacrylate and/or polymethacrylate; wherein the weight of the solid matrix expressed in weight % is in the range of from 80 to 90%, the weight of the first release controlling excipient is in the range of from 7 to 18%, and the weight of the second release controlling excipient is in the range of from 0.1 to 11%; or wherein the weight of the solid matrix is in the range of from 81 to 88%, the weight of the first release controlling excipient is in the range of from 8 to 17%, and the weight of the second release controlling excipient is in the range of from 0.5 to 10%; wherein the sum of the weights of the solid matrix and the first and the second release-controlling excipient equals 100%; wherein the coating further comprises one or more of triethylcitrate; polysorbate and/or talc; wherein the weight of neramexane, a pharmaceutically acceptable salt, solvate, conjugate, prodrug, polymorphic form, isomer, or derivative thereof embedded or dispersed in said solid matrix, ranges from 30 to 60 weight % or from 35 to 45 weight % based on the total weight of the solid matrix; and wherein the solid matrix further comprises one or more of microcrystalline cellulose; silica, talc; and/or magnesium stearate.

In another embodiment, the unit according to the invention comprises a solid matrix comprising neramexane, a pharmaceutically acceptable salt, solvate, conjugate, prodrug, polymorphic form, isomer, or derivative thereof embedded or dispersed in said solid matrix; wherein said solid matrix is coated with said at least one release-controlling excipient; wherein said at least one release-controlling excipient used for said coating comprises at least one first and at least one second release-controlling excipient, which are different from one another; wherein said at least one first release-controlling excipient is a polymer selected from polyacrylate and/or polymethacrylate; wherein said poly(meth)acrylate is an ester of poly(meth)acrylate; and wherein said second release controlling excipient is hydroxypropyl methylcellulose; and wherein the weight of the solid matrix expressed in weight % is in the range of from 80 to 90%, the weight of the first release controlling excipient is in the range of from 8 to 19%, and the weight of the second release controlling excipient is in the range of from 0.5 to 2%, wherein the sum of the weights of the solid matrix and the first and the second release-controlling excipient equals 100%.

In one embodiment, the weight of the solid matrix is in the range of from 81 to 88%, the weight of the first release controlling excipient is in the range of from 10 to 17%, and the weight of the second release controlling excipient is in the range of from 0.6 to 1.8%.

In one embodiment, the coating further comprises a plasticizer such as triethylcitrate; a stabilizer such as a polysorbate and/or an antisticking agent such as talc.

In one embodiment, the weight of neramexane, a pharmaceutically acceptable salt, solvate, conjugate, prodrug, polymorphic form, isomer, or derivative thereof embedded or dispersed in said solid matrix, ranges from 30 to 60 weight % or from 35 to 45 weight % based on the total weight of the solid matrix.

In one embodiment, the solid matrix further comprises a binder such as microcrystalline cellulose, a glidant such as silica or talc, and/or a lubricant such as magnesium stearate.

In one embodiment, said at least one release-controlling excipient used for said coating comprises at least one first and at least one second release-controlling excipient, which are different from one another; wherein said at least one first release-controlling excipient is a polymer selected from polyacrylate and/or polymethacrylate; wherein said poly(meth)acrylate is an ester of poly(meth)acrylate; and wherein said second release controlling excipient is hydroxypropyl methylcellulose; and wherein the weight of the solid matrix expressed in weight % is in the range of from 80 to 90%, the weight of the first release controlling excipient is in the range of from 8 to 19%, and the weight of the second release controlling excipient is in the range of from 0.5 to 2%; or wherein the weight of the solid matrix is in the range of from 81 to 88%, the weight of the first release controlling excipient is in the range of from 10 to 17%, and the weight of the second release controlling excipient is in the range of from 0.6 to 1.8%; wherein the sum of the weights of the solid matrix and the first and the second release-controlling excipient equals 100%; wherein the coating further comprises one or more of triethylcitrate; polysorbate and/or talc; and wherein the solid matrix further comprises one or more of microcrystalline cellulose; silica, talc; and/or magnesium stearate.

In still another embodiment, the unit according to the invention comprises a solid matrix comprising neramexane, a pharmaceutically acceptable salt, solvate, conjugate, prodrug, polymorphic form, isomer, or derivative thereof embedded or dispersed in said solid matrix; wherein said solid matrix is coated with said at least one release-controlling excipient; wherein said at least one release-controlling excipient used for said coating comprises at least one first and at least one second release-controlling excipient, which are different from one another; wherein said at least one first release-controlling excipient is ethylcellulose; and wherein said at least one second release-controlling excipient is a polyvinyl alcohol grafted with polyethylene glycol; and wherein the weight of the solid matrix expressed in weight % is in the range of from 80 to 90%, the weight of the first release controlling excipient is in the range of from 12 to 19%, and the weight of the second release controlling excipient is in the range of from 0.5 to 2%, wherein the sum of the weights of the solid matrix and the first and the second release-controlling excipient equals 100%.

In one embodiment, the weight of the solid matrix is in the range of from 81 to 84%, the weight of the first release controlling excipient is in the range of from 14 to 18%, and the weight of the second release controlling excipient is in the range of from 0.6 to 1.8%.

In one embodiment, the coating further comprises a plasticizer such as triethylcitrate; a stabilizer such as a polysorbate and/or an antisticking agent such as talc.

In one embodiment, the weight of neramexane, a pharmaceutically acceptable salt, solvate, conjugate, prodrug, polymorphic form, isomer, or derivative thereof embedded or dispersed in said solid matrix, ranges from 30 to 60 weight % or from 35 to 45 weight % based on the total weight of the solid matrix.

In one embodiment, the solid matrix further comprises a binder such as microcrystalline cellulose, a glidant such as silica or talc, and/or a lubricant such as magnesium stearate.

In one embodiment, said at least one release-controlling excipient used for said coating comprises at least one first and at least one second release-controlling excipient, which are different from one another; wherein said at least one first release-controlling excipient is ethylcellulose; and wherein said at least one second release-controlling excipient is a polyvinyl alcohol grafted with polyethylene glycol; and wherein the weight of the solid matrix expressed in weight % is in the range of from 80 to 90%, the weight of the first release controlling excipient is in the range of from 12 to 19%, and the weight of the second release controlling excipient is in the range of from 0.5 to 2%; or wherein the weight of the solid matrix is in the range of from 81 to 84%, the weight of the first release controlling excipient is in the range of from 14 to 18%, and the weight of the second release controlling excipient is in the range of from 0.6 to 1.8%; wherein the sum of the weights of the solid matrix and the first and the second release-controlling excipient equals 100%; wherein the coating further comprises one or more of triethylcitrate, polysorbate and/or talc; wherein the weight of neramexane, a pharmaceutically acceptable salt, solvate, conjugate, prodrug, polymorphic form, isomer, or derivative thereof embedded or dispersed in said solid matrix, ranges from 30 to 60 weight % or from 35 to 45 weight % based on the total weight of the solid matrix; and wherein the solid matrix further comprises one or more of microcrystalline cellulose; silica, talc; and/or magnesium stearate.

Release of the Active Agent from the Modified Release Dosage Form

A favorable feature of the modified release dosage form of the invention is the release of the active compound relatively independently of the pH of the dissolution medium.

In one embodiment, said period of time is substantially longer than about 30 minutes and shorter than 24 hours.

In another embodiment, said period is at least about 4 to 12 hours, as determined according to well-established and commonly accepted methods, e.g. by in-vitro dissolution testing according to the U.S. Pharmacopeia, USP 32, or the European Pharmacopeia, EP 5, using typical buffers with pH ranges of 1.0 to 7.2 as dissolution media. The methods are harmonized and the results are comparable. This definition is independent of the shape of the release profile, i.e. whether linear, curved according to first-order, second-order, or square root of time-kinetics, sigmoidal, etc. Accordingly, modified release should be understood to include extended release, prolonged release, sustained release, slow release and similar expressions for related drug release characteristics.

In one embodiment, the dosage form of the invention is a formulation that releases neramexane in a non-linear manner over a period of at least about 6 hours, with a release rate which decreases over time.

In another embodiment, neramexane is released in a substantially linear manner over at least 6 hours. The dissolution time for 50 wt.-% of the incorporated dose of the active compound to be released is typically at least 1 hour, and may be at least 1.5 hours.

In another embodiment the dissolution time for 40 wt.-% of the incorporated dose of the active compound to be released is typically at least 1 hour, and may be at least 1.5 hours.

In another embodiment the dissolution time for 60 wt.-% of the incorporated dose of the active compound to be released is typically at least 1 hour, and may be at least 1.5 hours. In another embodiment the dissolution time for 10 to 70 wt.-% of the incorporated dose of the active compound to be released is between about 1 and 8 hours.

In a further embodiment, the release is non-linear, and the dissolution time for 50 wt.-% of the incorporated dose of the active compound to be released is between about 1 and 5 hours, or between about 1 and 4 hours, or between about 1.5 and 3 hours. In contrast, if the release profile is substantially linear, then the dissolution time for 50 wt.-% of the dose is at least about 2 hours, or at least about 3 hours, such as about 4 hours to about 8 hours.

In one embodiment of the invention the in vitro active compound release profile is characterized by a dissolution time ranging from about 1 hour to about 3 hours for a fraction of 50 wt.-% of the amount of the active compound.

A non-linear release profile which is suitable for twice-daily and particularly once-daily dosing is further characterized by a dissolution time of 4 hours for a dose fraction ranging from about 50 wt.-% to about 95 wt.-% amount of the active compound.

In another embodiment, the dose fraction released after 4 hours ranges from about 65 wt.-% to about 95 wt.-%. In another embodiment, the dose fraction released after 4 hours ranges from about 55 wt.-% to about 85 wt.-%. Alternatively, the dose fraction released after 4 hours ranges from about 70 wt.-% to about 85 wt.-%. It has been found that such release behavior is useful for achieving and maintaining therapeutic plasma concentrations of neramexane in the steady state even with a single daily administration.

In another embodiment, a dose fraction ranging from about 75 wt.-% to about 95 wt.-% is released after a dissolution time of 6 hours, such as from about 80 wt.-% to about 90 wt.-%.

In one embodiment, said at least one release-controlling excipient is selected such that in application not more than 80% by weight of said active agent are released from said tablet within a period of 3 hours.

In another embodiment, said at least one release-controlling excipient is selected such that not more than 50% by weight are released within a period of 3 hours.

In another embodiment, said at least one release-controlling excipient is selected such that not more than 50% by weight are released within a period of 10 hours.

In one embodiment, only one release-controlling excipient is used as the at least one release-controlling excipient, i.e. the at least one release-controlling excipient comprises only one release-controlling excipient.

In another embodiment, the unit comprising the at least one release-controlling excipient comprising only one release-controlling excipient, releases the active agent after a retardation period within a short period nearly completely.

In one embodiment, such release profile may be characterized as a "pulsatile release profile".

The term "pulsatile release profile" encompasses a release profile where the active agent, e.g. neramexane, is released after a pronounced lag time followed by a rapid release phase of the active agent.

In one embodiment, wherein the at least one release-controlling excipient used for said coating, respectively the coating formed by the at least one release-controlling excipient, comprises at least one first and at least one second release-controlling excipient, wherein the first and the second release-controlling excipient are different from one another, said release-controlling excipients differ from one another with respect to the dissolution rate or swellability rate thereof in water or in a liquid comprising water.

In one embodiment, the at least one first release-controlling excipient is selected such that it has a slower dissolution rate or swellability rate in water or in a liquid comprising water than the at least one second release-controlling excipient.

In one embodiment, said dissolution rate or swellability rate of the at least one second release-controlling excipient is by a factor higher than the dissolution rate or swellability rate of the at least one first release-controlling excipient ranging from 2 to 1,000. In one embodiment, said factor ranges from 5 to 1,000, or from 10 to 1,000 or from 100 to 1,000.

In one embodiment, by means of selecting an appropriate factor, the dissolution profile of the unit in water or in a liquid comprising water, such as a body liquid, may be predetermined.

In one embodiment, wherein the factor is relatively low, after a lag time, the active agent may be released within a short period nearly completely.

Such release profile may be characterized as a "pulsatile release profile".

In one embodiment, it is possible to retard the release for e.g. 1 or two hours. This time may be sufficient to allow the unit to pass through the gastrointestinal tract of a human being after administration without an early release of the active agent. However, subsequent to the passing of the gastrointestinal tract, the active agent may be released nearly completely, e.g. in the small intestines, and may be provided in a concentration high enough to couple to respective receptors in order to effectively ameliorate a disorder such as tinnitus.

In another embodiment, wherein said factor is relatively high, after a lag time, the active agent may be released relatively continuously within an extended period. The release profile may be characterized by a "flat sigmoidal shape" or a "flat linear shape". Such profile is advantageous if a release profile is desired to provide a subject over an extended period of time with a relative constant and continuous amount of active agent.

The release profile may be adjusted by an appropriate selection of the first and second release-controlling excipient, the weight ratio of the excipients, the amount of said excipients in the unit, and the coating thickness.

The person skilled in the field of pharmaceutical formulations knows that it is surprising that a substance exhibiting a high solubility in water such as neramexane may be formulated such to exhibit a retarded release of the active agent. Moreover, the retardation may be adjusted in a tailor-made manner to specific needs of administration by employing the release-controlling excipients according to the invention providing for units as defined in the first to fifth and seventh aspect of the invention, wherein the units may be employed in the form of a modified release dosage form, which may be provided in the form of a multiple unit dosage form, a tablet or capsule or stickpack according to the sixth aspect of the invention.

Use of the Modified Release Dosage Form

In accordance with the present invention, a modified release dosage form such as a multiple unit dosage form such as tablets, granules or pellets, or a capsule or a stickpack comprising at least two tablets, granules or pellets is provided for the once daily administration of neramexane or a pharmaceutically acceptable salt thereof, to a human being or an animal subject.

The neramexane formulations of the invention are suitable for the treatment of diseases, including but not limited to the treatment of Alzheimer's disease, Parkinson's disease, AIDS dementia, neuropathic pain, diabetic neuropathic pain, cerebral ischemia, epilepsy, glaucoma, hepatic encephalopathy, multiple sclerosis, stroke, depression, tardive dyskinesia, amyotrophic lateral sclerosis, irritable bowel syndrome, appetite disorders, binge eating disorders, autism, attention deficit syndrome, attention deficit hyperactivity disorder, bipolar disorder, tinnitus, malaria, Borna virus, and Hepatitis C. Additional pathologies for treatment of which neramexane is suitable are disclosed in the art. Of particular interest is the ability to provide uninterrupted pain relief. Accordingly, the present invention further provides a method for the therapeutic or prophylactic treatment of disorders in a human or animal subject, the method including administering to the subject, a dosage form in accordance with the present invention.

The modified release dosage form or multiple unit dosage form or tablet or capsule or stickpack according to the invention comprising the units according to the invention, allows for an administration of the active agent to a subject in need thereof, which may provide for a relatively constant level of the active agent within the blood, respectively blood plasma, compared to an administration of a monolithic dosage form or single dosage form. Without being bound to a theory, it is believed that the success of the administration of a monolithic dosage form may strongly depend thereon whether the dosage form survives the passage through the gastrointestinal tract without early dissolution or not. Accordingly, the administration of such form may result in varying levels of the active agent within blood and blood plasma. Contrary to this, if a modified release dosage form or multiple unit dosage form, a tablet or a capsule or a stickpack according to the invention comprising a multitude of the units according to the invention is administered to a subject in need thereof, although some of the units may early dissolute within the gastrointestinal tract, a sufficient number of units will pass the gastrointestinal tract and will release the active agent such that within the blood, respectively blood plasma, a relatively constant level of active agent is maintained. This is an advantage over a conventional dosage form such as a monolithic dosage form or single dosage form.

EXAMPLES

Example 1

Dosage Form According to the Second Aspect of the Invention

Tablets

Tablets comprising approx. 2.5 mg neramexane mesylate are prepared as follows. The appropriate amount of neramexane mesylate, microcrystalline cellulose (Avicel PH 102), silica (Cab-O-Sil M5), magnesium stearate are weighed, and blended using a free fall blender (Bohle PTM 200). Alternatively the appropriate amounts of neramexane mesylate, microcrystalline cellulose, silica, magnesium stearate are sieved before being blended using the free fall blender. The powder are compressed into biconvex matrix tablets using a rotary tabletting press applying main compression forces of approx. 10 to 20 kN. An aqueous polymethacrylate dispersion (Eudragit® RS 30D) is sprayed onto the tablets. After drying, each tablet contains approx. 2.5 mg neramexane mesylate, 3.3 mg Avicel PH 102, 0.06 mg Cab-O-Sil M5, 0.12 mg magnesium stearate, 1.5 mg polymethacrylate. The total weight of the tablet is approx. 7.5 mg. The diameter is approx. 2 mm.

Tablets corresponding to a total amount of 50 mg neramexane mesylate are suspended in 900 ml phosphate buffer of pH 6.8. After stirring with baskets for 3 hours at 100 rpm, approx. 20% of the active agent is released.

Example 2

Dosage Form According to the Second Aspect of the Invention

Tablets

Tablets comprising approx. 2.5 mg neramexane mesylate are prepared as follows. The appropriate amount of neramexane mesylate, microcrystalline cellulose (Avicel PH 102), silica (Cab-O-Sil M5), magnesium stearate are weighed, and blended using a free fall blender (Bohle PTM 200). Alternatively the appropriate amounts of neramexane mesylate, microcrystalline cellulose, silica, magnesium stearate are sieved before being blended using the free fall blender. The powder are compressed into biconvex matrix tablets using a rotary tabletting press applying main compression forces of approx. 10 to 20 kN. An aqueous poly(meth)acrylate dispersion (Eudragit® NE 30) comprising talcum powder is sprayed onto the tablets. After drying, each tablet contains approx. 2.5 mg neramexane mesylate, 3.3 mg Avicel PH 102, 0.06 mg Cab-O-Sil M5, 0.12 mg magnesium stearate, 0.9 mg polymethacrylate and 0.9 mg talcum powder. The total weight of the tablet is approx. 7.8 mg. The diameter is approx. 2 mm.

Tablets corresponding to a total amount of 50 mg neramexane mesylate are suspended in 900 ml phosphate buffer of pH 6.8. After stirring with baskets for 3 hours at 100 rpm, approx. 13% of the active agent is released, after 10 hours about 70%.

Example 3

Tablets are prepared according to Example 2 with the difference that a tablet comprises 1.2 mg poly(meth)acrylate and 0.9 mg talcum. The release profile is determined according to the method of Example 2.

Example 4

Tablets are prepared according to Example 2 with the difference that a tablet comprises 0.6 mg poly(meth)acrylate and 0.6 mg talcum. The release profile is determined according to the method of Example 2.

Example 5

Tablets are prepared according to Example 2 with the difference that a tablet comprises 0.7 mg poly(meth)acrylate and 0.7 mg talcum. The release profile is determined according to the method of Example 2.

Example 6

Tablets are prepared according to Example 2 with the difference that a tablet comprises 1.8 mg poly(meth)acrylate and 0.8 mg talcum. The release profile is determined according to the method of Example 2.

The release profiles of the tablets prepared according to Examples 2 to 6 (Ex2 . . . Ex6) are compared in FIG. 1.

Example 7

Dosage Form According to the Second Aspect of the Invention

Granules

The recipe according to Example 1 is used for the preparation of granules. Granules are prepared by dry granulation. The appropriate amount of neramexane mesylate, microcrystalline cellulose (Avicel PH 102), silica (Cab-O-Sil M5), magnesium stearate are weighed and blended. The blend is fed to a laboratory compactor. The compacted product is granulated by using a fine granulator to granules having a diameter of approx. 1.5 mm. An aqueous polymethacrylate dispersion (Eudragit® RS 30) is sprayed (in a fluid bed reactor) onto the granules.

The granules have a release profile similar to the tablets of Example 1.

Example 8

Dosage Form According to the Third Aspect of the Invention

Tablets

Matrix tablets comprising approx. 1.0 mg neramexane mesylate are prepared as follows. The appropriate amount of neramexane mesylate, a blend of polyvinylpyrrolidone and polyvinyl acetate (here: Kollidon SR), silica (Cab-O-Sil M5), magnesium stearate are weighed, and blended using a free fall blender (Bohle PTM 200). Alternatively the appropriate amounts of neramexane mesylate, polyvinylpyrrolidone blend, silica, magnesium stearate are sieved before being blended using the free fall blender. The powder are compressed into biconvex matrix tablets using a rotary tabletting press applying main compression forces of approx. 3 to 20 kN. The diameter of the tablets is approx. 3 mm. Each tablet contains approx. 1.0 mg neramexane mesylate, 13.7 mg Kollidon SR, 0.15 mg Cab-O-Sil M5, 0.15 magnesium stearate.

Tablets corresponding to a total amount of 50 mg neramexane mesylate are suspended in 900 ml phosphate buffer of pH 6.8. After stirring with baskets for 3 hours at 100 rpm, approx. 80% of the active agent is released.

Example 9

Capsules Filled with an Amount of Approx. 200 Mg Modified Release Coated Spheres First layer (layer of active pharmaceutical ingredient (API)): Approx. 100 mg of spheres with a diameter of approx. 0.6 mm are sprayed with an aqueous solution containing 50 mg of API and 10 mg hydroxypropylcellulose.

Second layer (controlled release layer/membrane): Layered spheres are coated with a defined amount of Eudragit RL 30 D and/or Eudragit RS 30 D or Surelease to adjust the release profile.

A final polymer layer can be applied. Subsequently, the spheres are dried.

Example 10

Dosage Forms According to the Seventh Aspect of the Invention

Tablets

Tablets are prepared according to the method of Example 1, wherein the tablets comprise e.g. 2.5 my neramexane mesylate, 0.80 mg Eudragit RS 30D and 0.08 mg Eudragit RL 30D (ionic poly(meth)acrylates), 0.44 mg talc and 0.18 mg triethyl citrate in the coating. Eudragit RS 30D and 0.08 mg Eudragit RL 30D are applied in the form of a mixture by spraying.

Tablets corresponding to a total amount of 50 mg neramexane mesylate are suspended in 900 ml phosphate buffer of pH 6.8. After stirring with baskets at 100 rpm, approx. 5% of the active agent are released after 1 hour, 70% after 2 hours and nearly 100% after 3 hours. The release profile may be characterized as a "pulsatile release profile".

Example 11

Tablets are prepared according to Example 10 with the difference that a tablet comprises 1.20 mg Eudragit RS 30 D, 0.12 mg Eudragit RL 30 D, 0.66 mg talc, 0.27 mg triethylcitrate. The release profile is determined according to the method of Example 10.

Example 12

Tablets are prepared according to Example 10 with the difference that a tablet comprises 0.66 mg Eudragit RS 30 D, 0.66 mg Eudragit RL 30 D, 0.66 mg talc, 0.27 mg triethylcitrate. The release profile is determined according to the method of Example 10.

The release profiles of the tablets prepared according to Examples 10, 11 and 12 are compared in FIG. 2.

Example 13

Tablets are prepared according to the method of Example 1, wherein the tablets comprise e.g. 2.5 my neramexane mesylate, 0.96 mg Eudragit NE 30D (neutral poly(meth)acrylate), 0.96 mg talc, 0.096 mg polysorbate (commercially available under the trademark Montanox 80 PPI), and 0.096 mg hydroxypropylmethylcellulose (commercially available under the trademark Methocel E5 LV) in the coating. Eudragit NE 30D and hydroxypropylmethylcellulose are applied in the form of a mixture by spraying.

Tablets corresponding to a total amount of 50 mg neramexane mesylate are suspended in 900 ml phosphate buffer of pH 6.8. After stirring with baskets at 100 rpm, approx. 5% of the active agent are released after approx. 2 hours, 15% after 3 hours, 40% after 4 hours, 70% after 6 hours, 90% after 8 hours and nearly 100% after 10 hours. The release profile which may be characterized as a profile having a "flat sigmoidal shape".

Example 14

Tablets are prepared according to Example 13 with the difference that a tablet comprises 1.20 mg Eudragit NE 30D, 1.20 mg talcum, 0.12 mg polysorbate and 0.12 mg hydroxypropylmethylcellulose. The release profile is determined according to the method of Example 13.

Example 15

Tablets are prepared according to Example 13 with the difference that a tablet comprises 0.72 mg Eudragit NE 30D, 0.72 mg talcum, 0.072 mg polysorbate and 0.072 mg hydroxypropylmethylcellulose. The release profile is determined according to the method of Example 13.

Example 16

Tablets are prepared according to Example 13 with the difference that a tablet comprises 1.20 mg Eudragit NE 30D, 1.20 mg talcum, 0.12 mg polysorbate and 0.06 mg hydroxypropylmethylcellulose. The release profile is determined according to the method of Example 13.

The release profiles of the tablets prepared according to Examples 13 to 16 are compared in FIG. 3.

Example 17

Tablets are prepared according to the method of Example 1, wherein the tablets comprise e.g. 2.5 my neramexane mesylate, 1.2 mg ethylcellulose (commercially available under the trademark Aquacoat ECD), 0.36 mg triethyl citrate and 0.06 mg polyvinyl alcohol grafted with polyethylene glycol (commercially available under the trademark Kollicoat IR9).

Tablets corresponding to a total amount of 50 mg neramexane mesylate are suspended in 900 ml phosphate buffer of pH 6.8. After stirring with baskets at 100 rpm, approx. 15% of the active agent are released after approx. 6 hours, and 40% after 10 hours.

Example 18

Tablets are prepared according to Example 17 with the difference that a tablet comprises 1.20 mg ethylcellulose, 0.26 mg triethylcitrate and 0.06 mg polyvinyl alcohol grafted with polyethylene glycol. The release profile is determined according to the method of Example 17.

The release profiles of the tablets prepared according to Examples 17 and 18 are compared in FIG. 4.

Figure 1:
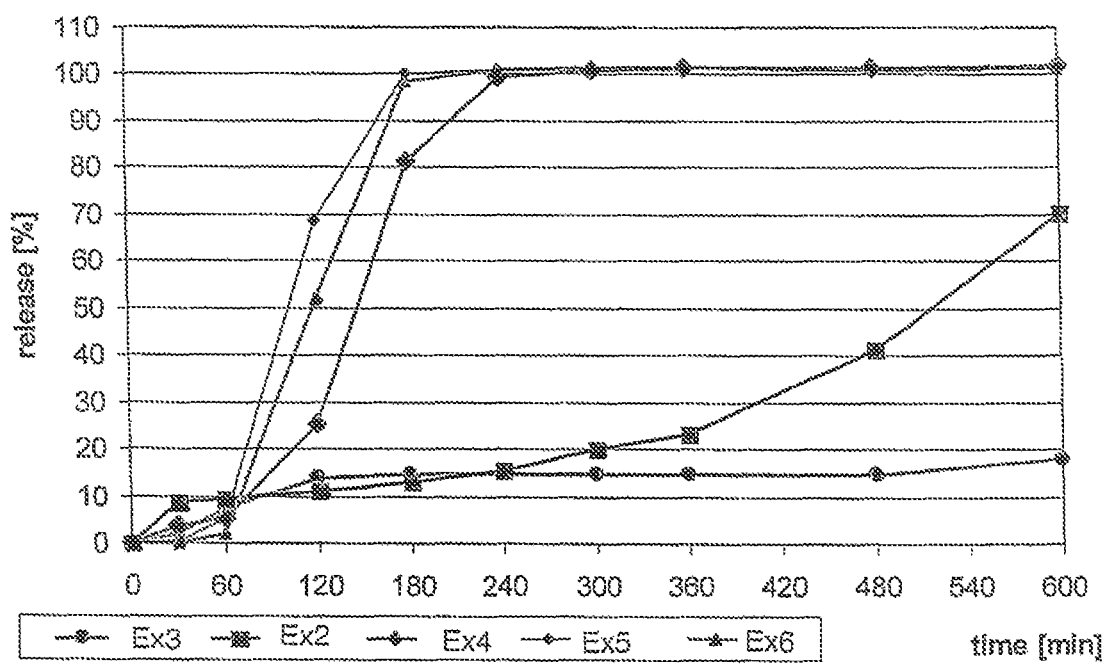
FIG. 1 shows a comparison of the release profiles of the tablets prepared according to Examples 2 to 6.
Figure 2:
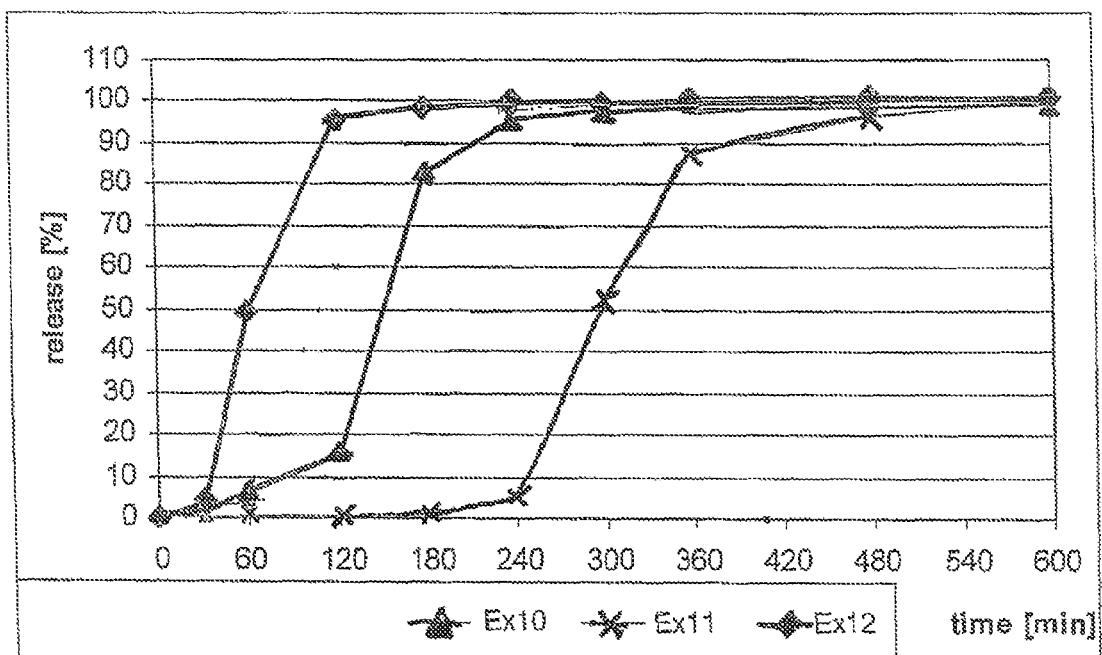
FIG. 2 shows a comparison of the release profiles of the tablets prepared according to Examples 10, 11 and 12.
Figure 3:
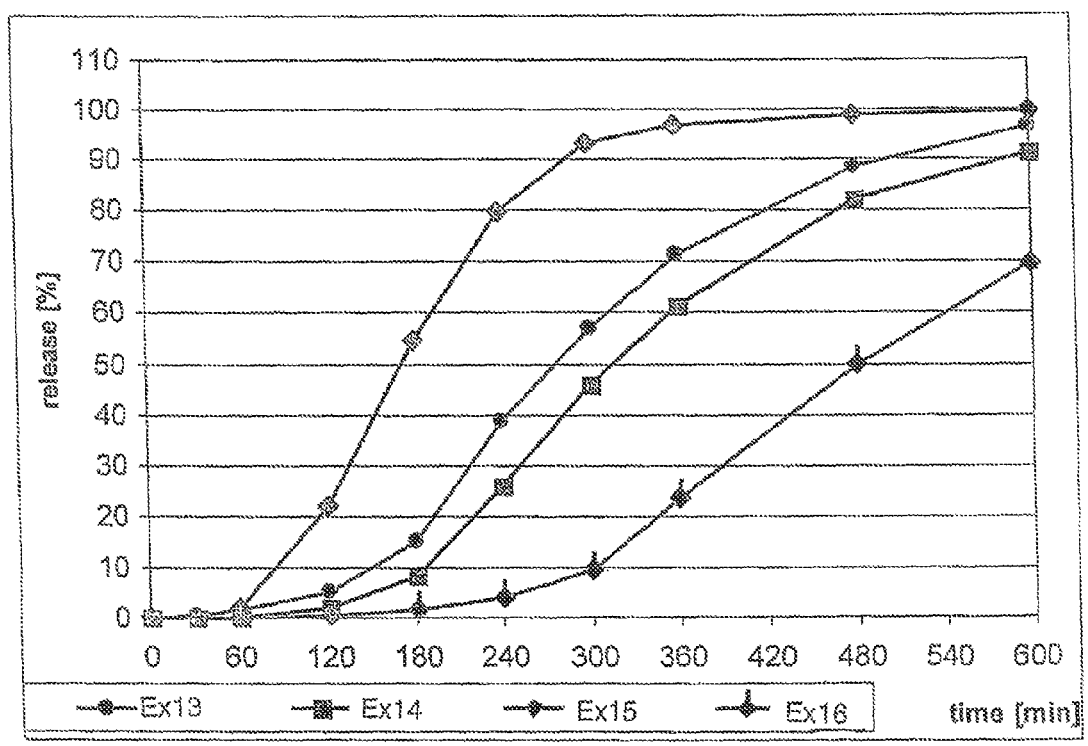
FIG. 3 shows a comparison of the release profiles of the tablets prepared according to Examples 13 to 16.
Figure 4:
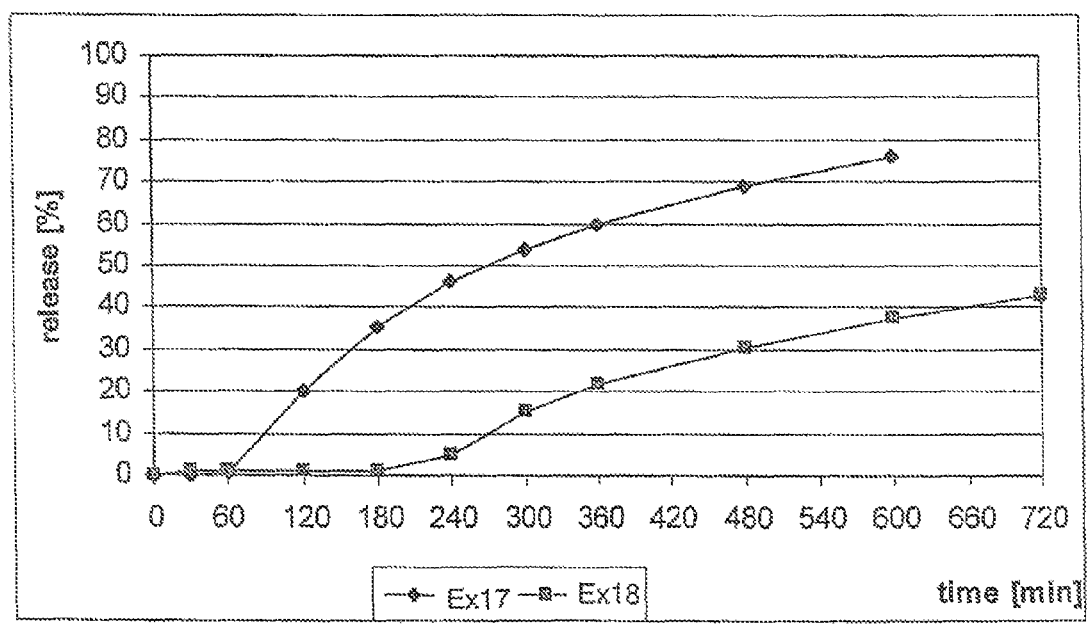
FIG. 4 shows a comparison of the release profiles of the tablets prepared according to Examples 17 and 18.

The invention claimed is:

1. A unit comprising neramexane, a pharmaceutically acceptable salt, solvate, conjugate, prodrug, polymorphic form, isomer, or derivative thereof; and at least one release-controlling excipient; wherein the unit has a diameter of from 0.1 to less than 6 mm,
  wherein
  the unit comprises a solid matrix comprising neramexane, a pharmaceutically acceptable salt, solvate, conjugate, prodrug, polymorphic form, isomer, or derivative thereof embedded or dispersed in the solid matrix;

wherein the solid matrix is coated with the at least one release-controlling excipient;

and wherein the at least one release-controlling excipient used for the coating comprises at least one first release-controlling excipient which is a non-ionic poly(meth)acrylate ester, and at least one second release-controlling excipient, which is hydroxypropylmethylcellulose, wherein the weight ratio of the at least one first release-controlling excipient to the at least one second release-controlling excipient is in the range of from 20:1 to 1:1:1 and the weight of the at least one first release-controlling excipient ranges from 2 to 25% based on the total weight of the unit.

2. The unit according to claim 1, wherein the unit is in the form of a tablet, granule, or pellet; or a combination of two or more thereof.

3. The unit according to claim 1, wherein the pharmaceutically acceptable salt is neramexane mesylate.

4. The unit according to claim 1, wherein not more than 50% by weight is released.

5. A modified release dosage form comprising at least one unit as defined in claim 1, or which is a multiple unit dosage form.

6. A tablet comprising at least two units as defined in claim 1, wherein the unit is a granule and/or a pellet.

7. A capsule or stickpack comprising at least one unit as defined in claim 1.

8. A capsule or stickpack comprising the modified release dosage form as defined in claim 5.

9. A capsule or stickpack comprising at least one tablet as defined in claim 6.

10. The unit according to claim 1, wherein the coating further comprises a sub-coating, an anti-sticking agent and/or a plasticizer.

11. The unit according to claim 1, wherein weight ratio of the at least one first release-controlling excipient to the at least one second release-controlling excipient is in the range of from 15:1 to 2:1.

\* \* \* \* \*